United States Patent
Choi et al.

(10) Patent No.: US 10,737,263 B2
(45) Date of Patent: Aug. 11, 2020

(54) ELECTRONIC LABEL-FREE DNA AND GENOME SEQUENCING

(71) Applicant: Roswell Biotechnologies, Inc., San Diego, CA (US)

(72) Inventors: Chulmin Choi, San Diego, CA (US); Sungho Jin, San Diego, CA (US); Paul W. Mola, San Diego, CA (US); Barry L. Merriman, San Diego, CA (US)

(73) Assignee: Roswell Biotechnologies, Inc., San Diego, CA (US)

(*) Notice: Subject to any disclaimer, the term of this patent is extended or adjusted under 35 U.S.C. 154(b) by 5 days.

(21) Appl. No.: 16/076,673

(22) PCT Filed: Feb. 9, 2017

(86) PCT No.: PCT/US2017/017231
§ 371 (c)(1),
(2) Date: Aug. 8, 2018

(87) PCT Pub. No.: WO2017/139493
PCT Pub. Date: Aug. 17, 2017

(65) Prior Publication Data
US 2019/0039065 A1  Feb. 7, 2019

Related U.S. Application Data

(60) Provisional application No. 62/293,239, filed on Feb. 9, 2016.

(51) Int. Cl.
*B01L 3/00* (2006.01)
*C12Q 1/6869* (2018.01)
(Continued)

(52) U.S. Cl.
CPC ... *B01L 3/502707* (2013.01); *B01L 3/502715* (2013.01); *C12Q 1/00* (2013.01);
(Continued)

(58) Field of Classification Search
CPC .... G01N 33/56; G01N 27/4035; B82Y 15/00; H01L 28/55
See application file for complete search history.

(56) References Cited

U.S. PATENT DOCUMENTS

| 5,082,627 A | 1/1992 | Stanbro |
| 5,194,133 A | 3/1993 | Clark et al. |

(Continued)

FOREIGN PATENT DOCUMENTS

| CN | 101231287 | 7/2008 |
| CN | 104685066 | 6/2015 |

(Continued)

OTHER PUBLICATIONS

USPTO; Non-Final Office Action dated Feb. 26, 2019 in U.S. Appl. No. 15/050,270.

(Continued)

*Primary Examiner* — Dah-Wei D. Yuan
*Assistant Examiner* — Andrew J Bowman
(74) *Attorney, Agent, or Firm* — Snell & Wilmer L.L.P.

(57) ABSTRACT

A method of manufacturing a device useable in DNA or genome sequencing comprises disposing pairs of electrodes on a substrate, the electrodes within each pair separated by a nanogap; depositing a resist layer over the electrodes; patterning the resist layer to create an exposed region on each electrode at or near each nanogap; roughening the electrode surface within each exposed region using various methods; and exposing the exposed regions to biomolecules, wherein one biomolecule bridges each nanogap of each electrode pair, with each end of each biomolecule bound to the electrodes at each exposed region.

25 Claims, 13 Drawing Sheets

(51) Int. Cl.
    *C12Q 1/00*            (2006.01)
    *G01N 27/327*       (2006.01)
    *C23C 14/16*         (2006.01)
    *C23C 14/48*         (2006.01)
    *C23F 4/00*           (2006.01)

(52) U.S. Cl.
    CPC ............ *C12Q 1/6869* (2013.01); *C23C 14/16* (2013.01); *C23C 14/48* (2013.01); *C23F 4/00* (2013.01); *G01N 27/3278* (2013.01); *B01L 2200/12* (2013.01); *B01L 2300/0645* (2013.01); *B01L 2300/0887* (2013.01); *B01L 2300/0896* (2013.01)

(56) References Cited

U.S. PATENT DOCUMENTS

| | | | |
|---|---|---|---|
| 5,366,140 A | 11/1994 | Koskenmaki et al. | |
| 5,414,588 A | 5/1995 | Barbee, Jr. | |
| 5,486,449 A | 1/1996 | Honso et al. | |
| 5,532,128 A | 7/1996 | Eggers et al. | |
| 5,583,359 A | 12/1996 | Ng et al. | |
| 5,639,507 A | 6/1997 | Galvagni et al. | |
| 5,767,687 A | 6/1998 | Geist | |
| 5,871,918 A | 2/1999 | Thorp et al. | |
| 5,881,184 A | 3/1999 | Guidash | |
| 5,982,018 A | 11/1999 | Wark | |
| 6,051,380 A | 4/2000 | Sosnowski et al. | |
| 6,060,023 A | 5/2000 | Maracas | |
| 6,094,335 A | 7/2000 | Early | |
| 6,110,354 A | 8/2000 | Saban | |
| 6,123,819 A | 9/2000 | Peeters | |
| 6,144,023 A | 11/2000 | Clerc | |
| 6,238,927 B1 | 5/2001 | Abrams et al. | |
| 6,440,662 B1 | 8/2002 | Gerwen et al. | |
| 6,464,889 B1 | 10/2002 | Lee et al. | |
| 6,506,564 B1 | 1/2003 | Mirkin et al. | |
| 6,537,747 B1 | 3/2003 | Mills, Jr. et al. | |
| 6,670,131 B2 | 12/2003 | Hashimoto | |
| 6,673,533 B1 | 1/2004 | Wohlstadter et al. | |
| 6,716,620 B2 | 4/2004 | Bashir et al. | |
| 6,749,731 B2 | 6/2004 | Kobori | |
| 6,762,050 B2 | 7/2004 | Fukushima et al. | |
| 6,764,745 B1 | 7/2004 | Karasawa et al. | |
| 6,790,341 B1 | 9/2004 | Saban | |
| 6,824,974 B2 | 11/2004 | Pisharody et al. | |
| 6,861,224 B2 | 3/2005 | Fujita et al. | |
| 6,916,614 B1 | 7/2005 | Takenaka et al. | |
| 6,958,216 B2 | 10/2005 | Kelley | |
| 7,015,046 B2 | 3/2006 | Wohlstadter et al. | |
| 7,075,428 B1 | 7/2006 | Oleynik | |
| 7,169,272 B2 | 1/2007 | Fritsch et al. | |
| 7,183,055 B2 | 2/2007 | Van Der Weide | |
| 7,189,435 B2 | 3/2007 | Tuominen et al. | |
| 7,202,480 B2 | 4/2007 | Yokoi et al. | |
| 7,208,077 B1 | 4/2007 | Albers et al. | |
| 7,276,206 B2 | 10/2007 | Augustine et al. | |
| 7,399,585 B2 | 7/2008 | Gau | |
| 7,432,120 B2 | 10/2008 | Mascolo et al. | |
| 7,470,533 B2 | 12/2008 | Xu et al. | |
| 7,507,320 B2 | 3/2009 | Hwang et al. | |
| 7,531,120 B2 | 5/2009 | Van Rijn et al. | |
| 7,579,823 B1 | 8/2009 | Ayliffe | |
| 7,691,433 B2 | 4/2010 | Kronholz et al. | |
| 7,785,785 B2 | 8/2010 | Pourmand et al. | |
| 7,834,344 B2 | 11/2010 | Mascolo et al. | |
| 7,851,045 B2 | 12/2010 | Gandon et al. | |
| 7,886,601 B2 | 2/2011 | Merassi et al. | |
| 7,901,629 B2 | 3/2011 | Calatzis et al. | |
| 7,943,394 B2 | 5/2011 | Flandre et al. | |
| 8,241,508 B2 | 8/2012 | D'Urso | |
| 8,351,181 B1 | 1/2013 | Ahn | |
| 8,591,816 B2 | 11/2013 | Calatzis et al. | |
| 8,652,768 B1 | 2/2014 | Huber et al. | |
| 8,753,893 B2 | 6/2014 | Liu et al. | |
| 8,927,464 B2 | 1/2015 | Aizenberg et al. | |
| 8,940,663 B2 | 1/2015 | Iqbal et al. | |
| 9,108,880 B2 | 8/2015 | Jin et al. | |
| 9,306,164 B1 | 4/2016 | Chang et al. | |
| 9,829,456 B1 | 11/2017 | Merriman et al. | |
| 9,956,743 B2 | 5/2018 | Jin et al. | |
| 10,036,064 B2 | 7/2018 | Merriman et al. | |
| 10,125,420 B2 | 11/2018 | Jin et al. | |
| 10,151,722 B2 | 12/2018 | Jin et al. | |
| 10,508,296 B2 | 12/2019 | Merriman et al. | |
| 10,526,696 B2 | 1/2020 | Jin et al. | |
| 10,584,410 B2 | 3/2020 | Jin et al. | |
| 10,597,767 B2 | 3/2020 | Merriman et al. | |
| 2002/0022223 A1 | 2/2002 | Connolly | |
| 2002/0090649 A1 | 7/2002 | Chan et al. | |
| 2002/0137083 A1 | 9/2002 | Kobori et al. | |
| 2002/0138049 A1 | 9/2002 | Allen et al. | |
| 2002/0142150 A1 | 10/2002 | Baumann et al. | |
| 2002/0142477 A1 | 10/2002 | Lewis et al. | |
| 2002/0172963 A1 | 11/2002 | Kelley et al. | |
| 2002/0184939 A1 | 12/2002 | Yadav | |
| 2003/0025133 A1 | 2/2003 | Brousseau | |
| 2003/0040000 A1 | 2/2003 | Connolly et al. | |
| 2003/0064390 A1 | 4/2003 | Schülein et al. | |
| 2003/0087296 A1 | 5/2003 | Fujita et al. | |
| 2003/0186263 A1 | 10/2003 | Frey et al. | |
| 2003/0224387 A1 | 12/2003 | Kunwar et al. | |
| 2004/0014106 A1 | 1/2004 | Patno et al. | |
| 2004/0023253 A1 | 2/2004 | Kunwar et al. | |
| 2004/0038090 A1 | 2/2004 | Faris | |
| 2004/0063100 A1 | 4/2004 | Wang | |
| 2004/0086929 A1 | 5/2004 | Weide et al. | |
| 2004/0096866 A1 | 5/2004 | Hoffman et al. | |
| 2004/0012161 A1 | 6/2004 | Chiu | |
| 2004/0146863 A1 | 7/2004 | Pisharody et al. | |
| 2004/0209355 A1 | 10/2004 | Edman et al. | |
| 2004/0209435 A1 | 10/2004 | Patridge et al. | |
| 2004/0235016 A1 | 11/2004 | Hamers | |
| 2004/0248282 A1* | 12/2004 | Sobha | G11C 13/0014 435/287.2 |
| 2005/0029227 A1 | 2/2005 | Chapman | |
| 2005/0067086 A1 | 3/2005 | Ito et al. | |
| 2005/0074911 A1 | 4/2005 | Kornilovich et al. | |
| 2005/0151541 A1 | 7/2005 | Brinz et al. | |
| 2005/0172199 A1 | 8/2005 | Miller et al. | |
| 2005/0181195 A1 | 8/2005 | Dubrow | |
| 2005/0221473 A1 | 10/2005 | Dubin et al. | |
| 2005/0227373 A1 | 10/2005 | Flandre et al. | |
| 2005/0247573 A1 | 11/2005 | Nakamura et al. | |
| 2005/0285275 A1 | 12/2005 | Son | |
| 2005/0287548 A1 | 12/2005 | Bao et al. | |
| 2005/0287589 A1 | 12/2005 | Connolly | |
| 2006/0003482 A1 | 1/2006 | Chinthakindi et al. | |
| 2006/0019273 A1 | 1/2006 | Connolly et al. | |
| 2006/0024504 A1 | 2/2006 | Nelson et al. | |
| 2006/0024508 A1 | 2/2006 | D'Urso et al. | |
| 2006/0029808 A1 | 2/2006 | Zhai et al. | |
| 2006/0051919 A1 | 3/2006 | Mascolo et al. | |
| 2006/0051946 A1 | 3/2006 | Mascolo et al. | |
| 2006/0105449 A1 | 5/2006 | Larmer et al. | |
| 2006/0105467 A1 | 5/2006 | Niksa et al. | |
| 2006/0128239 A1 | 5/2006 | Nun et al. | |
| 2006/0147983 A1 | 7/2006 | O'uchi | |
| 2006/0154489 A1 | 7/2006 | Tornow | |
| 2006/0275853 A1 | 12/2006 | Matthew et al. | |
| 2007/0026193 A1 | 2/2007 | Luzinov et al. | |
| 2007/0048748 A1 | 3/2007 | Williams et al. | |
| 2007/0140902 A1 | 6/2007 | Calatzis et al. | |
| 2007/0148815 A1 | 6/2007 | Chao et al. | |
| 2007/0184247 A1 | 9/2007 | Simpson et al. | |
| 2007/0207487 A1 | 9/2007 | Emig et al. | |
| 2007/0231542 A1 | 10/2007 | Deng | |
| 2008/0098815 A1 | 5/2008 | Merassi et al. | |
| 2008/0199657 A1 | 8/2008 | Capron et al. | |
| 2008/0199659 A1 | 8/2008 | Zhao | |
| 2009/0011222 A1 | 1/2009 | Xiu et al. | |
| 2009/0017571 A1 | 1/2009 | Nuckolls | |
| 2009/0020428 A1 | 1/2009 | Levitan | |

(56) References Cited

U.S. PATENT DOCUMENTS

| | | |
|---|---|---|
| 2009/0027036 A1* | 1/2009 | Nuckolls .............. G01N 33/5438 324/76.11 |
| 2009/0062684 A1 | 3/2009 | Gregersen et al. |
| 2009/0152109 A1 | 6/2009 | Whitehead et al. |
| 2009/0170716 A1 | 7/2009 | Su et al. |
| 2009/0178935 A1 | 7/2009 | Reymond et al. |
| 2009/0295372 A1 | 12/2009 | Krstic et al. |
| 2009/0297913 A1 | 12/2009 | Zhang et al. |
| 2009/0306578 A1 | 12/2009 | Sivan et al. |
| 2009/0324308 A1 | 12/2009 | Law et al. |
| 2010/0038342 A1 | 2/2010 | Lim et al. |
| 2010/0044212 A1 | 2/2010 | Kim et al. |
| 2010/0055397 A1 | 3/2010 | Kurihara et al. |
| 2010/0132771 A1 | 6/2010 | Lu |
| 2010/0142259 A1 | 6/2010 | Drndic et al. |
| 2010/0149530 A1 | 6/2010 | Tomaru |
| 2010/0167938 A1 | 7/2010 | Su et al. |
| 2010/0184062 A1 | 7/2010 | Steinmueller-Nethl et al. |
| 2010/0188109 A1 | 7/2010 | Edel et al. |
| 2010/0194409 A1 | 8/2010 | Gao et al. |
| 2010/0206367 A1 | 8/2010 | Jeong et al. |
| 2010/0280397 A1 | 11/2010 | Feldman et al. |
| 2010/0285275 A1 | 11/2010 | Baca et al. |
| 2010/0285601 A1 | 11/2010 | Kong et al. |
| 2010/0288543 A1 | 11/2010 | Hung et al. |
| 2010/0300899 A1 | 12/2010 | Levine et al. |
| 2011/0056845 A1 | 3/2011 | Stellacci et al. |
| 2011/0076783 A1 | 3/2011 | Liu et al. |
| 2011/0091787 A1 | 4/2011 | McGrath et al. |
| 2011/0160077 A1 | 6/2011 | Chaisson et al. |
| 2011/0166034 A1 | 7/2011 | Kwong et al. |
| 2011/0217763 A1 | 9/2011 | Rasooly et al. |
| 2011/0227558 A1 | 9/2011 | Mannion et al. |
| 2011/0229667 A1 | 9/2011 | Jin et al. |
| 2011/0233075 A1 | 9/2011 | Soleymani et al. |
| 2011/0287956 A1 | 11/2011 | Iqbal et al. |
| 2011/0291673 A1 | 12/2011 | Shibata et al. |
| 2011/0311853 A1 | 12/2011 | Fratti |
| 2011/0312529 A1 | 12/2011 | He et al. |
| 2012/0060905 A1 | 3/2012 | Fogel et al. |
| 2012/0220046 A1 | 8/2012 | Chao |
| 2012/0258870 A1 | 10/2012 | Schwartz et al. |
| 2012/0286332 A1 | 11/2012 | Rothberg et al. |
| 2013/0049158 A1 | 2/2013 | Hong et al. |
| 2013/0108956 A1 | 5/2013 | Lu et al. |
| 2013/0109577 A1 | 5/2013 | Korlach et al. |
| 2013/0162276 A1 | 6/2013 | Lee et al. |
| 2013/0183492 A1 | 7/2013 | Lee et al. |
| 2013/0214875 A1 | 8/2013 | Duncan et al. |
| 2013/0239349 A1 | 9/2013 | Knights et al. |
| 2013/0245416 A1 | 9/2013 | Yarmush et al. |
| 2013/0273340 A1 | 10/2013 | Neretina et al. |
| 2013/0281325 A1 | 10/2013 | Elibol et al. |
| 2013/0331299 A1 | 12/2013 | Reda et al. |
| 2014/0001055 A1 | 1/2014 | Elibol et al. |
| 2014/0011013 A1 | 1/2014 | Jin |
| 2014/0018262 A1 | 1/2014 | Reda et al. |
| 2014/0027775 A1 | 1/2014 | Quick et al. |
| 2014/0048776 A1 | 2/2014 | Huang et al. |
| 2014/0057283 A1 | 2/2014 | Wang et al. |
| 2014/0061049 A1 | 3/2014 | Lo et al. |
| 2014/0079592 A1 | 3/2014 | Chang et al. |
| 2014/0170567 A1 | 6/2014 | Sakamoto et al. |
| 2014/0174927 A1 | 6/2014 | Bashir et al. |
| 2014/0197459 A1 | 7/2014 | Kis et al. |
| 2014/0218637 A1 | 8/2014 | Gao et al. |
| 2014/0235493 A1 | 8/2014 | Zang et al. |
| 2014/0253827 A1 | 9/2014 | Gao et al. |
| 2014/0284667 A1 | 9/2014 | Basker et al. |
| 2014/0367749 A1 | 12/2014 | Bai et al. |
| 2014/0377900 A1* | 12/2014 | Astier .............. G01N 33/48721 438/49 |
| 2015/0005188 A1 | 1/2015 | Levner et al. |
| 2015/0017655 A1 | 1/2015 | Huang et al. |
| 2015/0049332 A1 | 2/2015 | Sun et al. |
| 2015/0057182 A1 | 2/2015 | Merriman et al. |
| 2015/0068892 A1 | 3/2015 | Ueno et al. |
| 2015/0148264 A1 | 5/2015 | Esfandyarpour et al. |
| 2015/0177150 A1 | 6/2015 | Rothberg et al. |
| 2015/0191709 A1 | 7/2015 | Heron et al. |
| 2015/0263203 A1 | 9/2015 | Lewis et al. |
| 2015/0293025 A1 | 10/2015 | Ninomiya et al. |
| 2015/0294875 A1 | 10/2015 | Khondaker et al. |
| 2015/0344945 A1 | 12/2015 | Mandell et al. |
| 2016/0017416 A1 | 1/2016 | Boyanov et al. |
| 2016/0045378 A1 | 2/2016 | Geloen |
| 2016/0155971 A1 | 6/2016 | Strachan et al. |
| 2016/0187282 A1 | 6/2016 | Gardner et al. |
| 2016/0284811 A1 | 9/2016 | Yu et al. |
| 2016/0319342 A1 | 11/2016 | Kawai et al. |
| 2016/0377564 A1 | 12/2016 | Carmignani et al. |
| 2017/0023512 A1 | 1/2017 | Cummins et al. |
| 2017/0037462 A1 | 2/2017 | Turner et al. |
| 2017/0043355 A1 | 2/2017 | Fischer |
| 2017/0044605 A1 | 2/2017 | Merriman |
| 2017/0131237 A1 | 5/2017 | Ikeda |
| 2017/0184542 A1 | 6/2017 | Chatelier et al. |
| 2017/0234825 A1 | 8/2017 | Elibol et al. |
| 2017/0240962 A1 | 8/2017 | Merriman |
| 2017/0332918 A1 | 11/2017 | Keane |
| 2018/0014786 A1 | 1/2018 | Keane |
| 2018/0031508 A1 | 2/2018 | Jin |
| 2018/0031509 A1 | 2/2018 | Jin |
| 2018/0045665 A1 | 2/2018 | Jin |
| 2018/0259474 A1 | 9/2018 | Jin |
| 2018/0297321 A1 | 10/2018 | Jin et al. |
| 2018/0305727 A1 | 10/2018 | Merriman |
| 2018/0340220 A1 | 11/2018 | Merriman |
| 2019/0004003 A1 | 1/2019 | Merriman |
| 2019/0033244 A1 | 1/2019 | Jin |
| 2019/0041355 A1 | 2/2019 | Merriman |
| 2019/0041378 A1 | 2/2019 | Choi |
| 2019/0094175 A1 | 3/2019 | Merriman |
| 2019/0194801 A1 | 6/2019 | Jin et al. |
| 2019/0355442 A1 | 11/2019 | Merriman et al. |
| 2019/0376925 A1 | 12/2019 | Choi et al. |
| 2019/0383770 A1 | 12/2019 | Choi et al. |

FOREIGN PATENT DOCUMENTS

| | | |
|---|---|---|
| CN | 104703700 | 6/2015 |
| CN | 108027335 | 5/2018 |
| DE | 102012008375 | 10/2012 |
| DE | 102013012145 | 1/2015 |
| EP | 2053383 | 4/2009 |
| EP | 3403079 | 11/2018 |
| EP | 3408219 | 12/2018 |
| EP | 3408220 | 12/2018 |
| EP | 3414784 | 12/2018 |
| EP | 3420580 | 1/2019 |
| JP | 2018-522236 | 8/2018 |
| KR | 20070059880 | 6/2007 |
| KR | 20110104245 | 9/2011 |
| WO | 2002049980 | 6/2002 |
| WO | 2002074985 | 9/2002 |
| WO | 2003042396 | 5/2003 |
| WO | 2004096986 | 11/2004 |
| WO | 2004099307 | 11/2004 |
| WO | 2005108612 | 11/2005 |
| WO | 2007054649 | 5/2007 |
| WO | 2007102960 | 9/2007 |
| WO | 2007126432 | 11/2007 |
| WO | 2007128965 | 11/2007 |
| WO | 2009003208 | 1/2009 |
| WO | 2010022107 | 2/2010 |
| WO | 2012083249 | 6/2012 |
| WO | 2012087352 | 6/2012 |
| WO | 2012152056 | 11/2012 |
| WO | 2013096851 | 6/2013 |
| WO | 2014182630 | 7/2014 |
| WO | 2015167019 | 11/2015 |
| WO | 2015176990 | 11/2015 |
| WO | 2015188197 | 12/2015 |
| WO | 2016016635 | 2/2016 |

(56) References Cited

FOREIGN PATENT DOCUMENTS

| WO | 2016100637 | 6/2016 |
| --- | --- | --- |
| WO | 2016196755 | 12/2016 |
| WO | 2016210386 | 12/2016 |
| WO | 2017042038 | 3/2017 |
| WO | 2017061129 | 4/2017 |
| WO | 2017123416 | 7/2017 |
| WO | 2017132567 | 8/2017 |
| WO | 2017132586 | 8/2017 |
| WO | 2017139493 | 8/2017 |
| WO | 2017147187 | 8/2017 |
| WO | 2017151680 | 9/2017 |
| WO | 2017184677 | 10/2017 |
| WO | 2018022799 | 2/2018 |
| WO | 2018026855 | 2/2018 |
| WO | 2018098286 | 5/2018 |
| WO | 2018132457 | 7/2018 |
| WO | 2018136148 | 7/2018 |
| WO | 2018200687 | 11/2018 |
| WO | 2018208505 | 11/2018 |

OTHER PUBLICATIONS

USPTO; Final Office Action dated Mar. 1, 2019 in U.S. Appl. No. 15/979,135.
USPTO; Non-Final Office Action dated Mar. 6, 2019 in U.S. Appl. No. 16/015,049.
USPTO; Non-Final Office Action dated Mar. 7, 2019 in U.S. Appl. No. 15/944,356.
USPTO; Final Office Action dated Apr. 15, 2019 in U.S. Appl. No. 16/015,028.
Antibody Structure Downloaded from https://absoluteantibody.com/antibody-resources/antibody-overview/antibody-structure/ (Mar. 1, 2019).
Bai et al., "Review: Gas Sensors Based on Conducting Polymers," Sensors, vol. 7, pp. 267-307, (2007).
Bailey et al., "DNA-Encoded Antibody Libraries: A Unified Platform for Multiplexed Cell Sorting and Detection of Genes and Proteins," Journal of Am Chem Soc, vol. 129, pp. 1959-1967, (2007).
Khawli et al., "Charge Variants in IgG1-Isolation, Characterization, In Vitro Binding Properties and Pharmacokinetics in Rats," Landes Bioscience, pp. 613-623, (2010).
Schaefer et al., "Stability and Dewetting Kinetics of Thin Gold Films on Ti, TiOx, and ZnO Adhesion Layers," Acta Materialia, vol. 61, pp. 7841-7848, (2013).
USPTO; Requirement for Restriction dated Jan. 17, 2017 in U.S. Appl. No. 15/336,557.
USPTO; Advisory Action dated Mar. 14, 2017 in U.S. Appl. No. 15/050,270.
USPTO; Non-Final Office Action dated May 16, 2017 in U.S. Appl. No. 15/336,557.
USPTO; Final Office Action dated Dec. 30, 2016 in U.S. Appl. No. 15/050,270.
USPTO; Non-Final Office Action dated Sep. 29, 2017 in U.S. Appl. No. 15/050,270.
USPTO; Non-Final Office Action dated Oct. 19, 2016 in U.S. Appl. No. 15/220,307.
USPTO; Notice of Allowance dated Jul. 28, 2017 in U.S. Appl. No. 15/220,307.
USPTO; Requirement for Restriction dated Dec. 1, 2016 in U.S. Appl. No. 13/996,477.
USPTO; Non-Final Office Action dated May 5, 2017 in U.S. Appl. No. 13/996,477.
USPTO; Final Office Action dated Oct. 4, 2017 in U.S. Appl. No. 13/996,477.
USPTO; Notice of Allowance dated Jan. 3, 2018 in U.S. Appl. No. 13/996,477.
USPTO; Non-Final Office Action dated Feb. 9, 2018 in U.S. Appl. No. 15/728,400.
USPTO; Non-Final Office Action dated Feb. 23, 2018 in U.S. Appl. No. 15/728,412.
USPTO; Non-Final Office Action dated Feb. 23, 2018 in U.S. Appl. No. 15/796,080.
USPTO; Final Office Action dated Mar. 8, 2018 in U.S. Appl. No. 15/336,557.
USPTO; Notice of Allowance dated May 25, 2018 in U.S. Appl. No. 15/336,557.
USPTO; Final Office Action dated Jun. 13, 2018 in U.S. Appl. No. 15/728,412.
USPTO; Final Office Action dated Jun. 14, 2018 in U.S. Appl. No. 15/796,080.
USPTO; Final Office Action dated Jul. 10, 2018 in U.S. Appl. No. 15/050,270.
USPTO; Final Office Action dated Jul. 10, 2018 in U.S. Appl. No. 15/728,400.
PCT; International Search Report and Written Opinion dated Apr. 8, 2010 in Application No. PCT/US2009/054235.
PCT; International Search Report and Written Opinion dated Nov. 29, 2012 in Application No. PCT/US2011/001995.
PCT; International Search Report and Written Opinion dated Sep. 27, 2016 in Application No. PCT/US2016/039446.
PCT; International Search Report and Written Opinion dated May 25, 2017 in Application No. PCT/US2017/18950.
PCT; International Search Report and Written Opinion dated Jul. 26, 2017 in Application No. PCT/US2017/017231.
PCT; International Search Report and Written Opinion dated Apr. 18, 2017 in Application No. PCT/US2016/068922.
PCT; International Search Report and Written Opinion dated Jan. 27, 2017 in Application No. PCT/US2017/015465.
PCT; International Search Report and Written Opinion dated Jan. 27, 2017 in Application No. PCT/US2017/015437.
PCT; International Search Report and Written Opinion dated Nov. 22, 2017 in Application No. PCT/US2017/044023.
PCT; International Search Report and Written Opinion dated Dec. 26, 2017 in Application No. PCT/US2017/044965.
PCT; International Search Report and Written Opinion dated Mar. 7, 2018 in Application No. PCT/US2017/063105.
PCT; International Search Report and Written Opinion dated Mar. 12, 2018 in Application No. PCT/US2017/063025.
PCT; International Search Report and Written Opinion dated Apr. 13, 2018 in Application No. PCT/US2018/013140.
PCT; International Search Report and Written Opinion dated Jul. 20, 2018 in Application No. PCT/US2018/029382.
PCT; International Search Report and Written Opinion dated Jul. 20, 2018 in Application No. PCT/US2018/029393.
Fink et al., "Electrical Conduction Through DNA Molecules," Nature, vol. 398, pp. 407-410, (Jan. 20, 1999).
Stenning, "The Investigation of Grain Boundary Development and Crystal Synthesis of Thin Gold Films on Silicon Wafers," http://www.ucl.ac.uk/~ucapikr/projects, (Mar. 31, 2009).
Bechelany et al., "Synthesis Mechanisms of Organized Nanoparticles: Influence of Annealing Temperature and Atmosphere," Crystal Growth and Design, vol. 10, pp. 587-596, (Oct. 21, 2010).
H. Nishida, et al., "Self-Oriented Immobilization of DNA Polymerase Tagged by Titanium-Binding Peptide Motif," Langmuir, vol. 31, pp. 732-740, (Dec. 17, 2014).
Niwa, O. et al., "Fabrication and Characteristics of Vertically Separated Interdigitated Array Electrodes," Journal of Electroanalytical Chemistry and Interfacial Electrochemistry, vol. 267, pp. 291-297, (Aug. 10, 1989) (Abstract Only).
Park, S.J. et al., "Array-Based Electrical Detection of DNA with Nanoparticle Probes," Science, vol. 295, pp. 1503-1506, (Feb. 22, 2002).
Urban, M. et al., "A Paralleled Readout System for an Electrical DNA-Hybridization Assay Based on a Microstructured Electrode Array," Review of Scientific Instruments, vol. 74, pp. 1077-1081, (Jan. 2003) (Abstract Only).
Choi Y.S. et al., "Hybridization by an Electroatomical Genome on Detection on Using an Indicator-Free DNA on a Microelectrode-Array DNA Chip," Bulletin of the Korean Chemistry Society, vol. 26, pp. 379-383, (2005).

(56) References Cited

OTHER PUBLICATIONS

Park, C.W. et al., "Fabrication of Poly-Si/ AU Nano-Gaps Using Atomic-Layer-Deposited $Al_2O_3$ as a Sacrificial Layer," Nanotechnology, vol. 16, pp. 361-364, (Feb. 1, 2005) (Abstract Only).
Ruttkowski, E. et al., "CMOS Based Arrays of Nanogaps Devices for Molecular Devices," Proceedings of 2005 5th IEEE Conference on Nanotechnology, vol. 1, pp. 438-441, (Jul. 2005) (Abstract Only).
Stagni, C. et al., "CMOS DNA Sensor Array with Integrated A/D Conversation Based on Label-Free Capacitance Measurement," IEEE Journal of Solid-State Circuits, vol. 41, pp. 2956-2964, (Nov. 20, 2006).
Schrott, W. et al., "Metal Electrodes in Plastic Microfluidic Systems," Microelectronic Engineering, vol. 86, pp. 1340-1342, (Jun. 2009).
Roy, S. et al., "Mass-Produced Nanogap Sensor Arrays for Ultra-Sensitive Detection of DNA," Journal of the American Chemical Society, vol. 131, pp. 12211-12217, (Aug. 5, 2009) (Abstract Only).
Choi, J. E. et al., "Fabrication of Microchannel with 60 Electrodes and Resistance Measurement," Flow Measurement and Instrumentation, vol. 21, pp. 178-183, (Sep. 2010) (Abstract Only).
Lee, K. H. et al., "One-Chip Electronic Detection of DNA Hybridization using Precision Impedance-Based CMOS Array Sensor," Biosensors and Bioelectronics, vol. 26, pp. 1373-1379, (Dec. 15, 2010).
Chen, X. et al., "Electrical Nanogap Devices for Biosensing," Materials Today, vol. 13, pp. 28-41, (Nov. 2010).
Ghindilis, A. et al., "Real Time Biosensor Platforms Fully Integrated Device for Impedimetric Assays," ECS Transactions, vol. 33, pp. 59-68, (2010).
Su, Y., "Modeling and Characteristic Study of Thin Film Based Biosensor Based on COMSOL," Mathematical Problems in Engineering, Article 581063 (6 Pages), (Apr. 7, 2014).
Blossey, R., "Self-Cleaning Surfaces—Virtual Realities," Nature Materials, vol. 2(5), pp. 301-306, (May 2006).
Cassie, A.B.D. et al., "Wettability of Porous Surfaces," Transitions of the Faraday Society, vol. 40, pp. 546-551, (Jan. 1944) (Abstract Only).
Choi, C. et al., "Strongly Superhydrophobic Silicon Nanowires by Supercritical CO2 Drying," Electronic Materials Letters, vol. 6 (2), pp. 59-64, (Jun. 2010).
Coulson S.R. et al., "Super-Repellent Composite Fluoropolymer Surfaces," The Journal of Physical Chemistry B., vol. 104(37), pp. 8836-8840, (Aug. 2000).
Gapin, A.I. et al., "CoPt Patterned Media in Anodized Aluminum Oxide Templates," Journal of Applied Physics, vol. 99(8), pp. 08G902 (1-3), (Apr. 2006).
Parkin, I. P. et al., "Self-Cleaning Coatings," Journal of Materials Chemistry, vol. 15(17), pp. 1689-1695, (Dec. 2004).
Shimoda, T. et al., "Solution-Processed Silicon Films and Transistors," Nature, vol. 440(7085), pp. 783-786, (Apr. 2006).
Kim, J. Y. et al., "Optically Transparent Glass with Vertically Aligned Surface Al2O3 Nanowires Having Superhydrophobic Characteristics," NANO: Brief Reports and Reviews, vol. 5(2), pp. 89-95, (Apr. 2010) (Abstract Only).
Han, "Energy Band Gap Engineering of Graphene Nanoribbons," Physical Review Letters, vol. 98, pp. 1-7, (May 16, 2007).
Prins et al., "Room-Temperature Gating of Molecular Junctions Using Few-Layer Graphene Nanogap Electrodes," Nano Letters, vol. 11, pp. 4607-4611, (Oct. 21, 2011).
Heerema et al., "Graphene Nanodevices for DNA Sequencing," Nature Nanotechnology, vol. 11, pp. 127-136, (Feb. 3, 2016).
Liu et al., "Atomically Thin Molybdenum Disulfide Nanopores with High Sensitivity for DNA Translocation," ACS Nano, vol. 8, pp. 2504-2511, (Feb. 18, 2014).
Kim et al., "Rapid Fabrication of Uniformly Sized Nanopores and Nanopore Arrays for Parallel DNA Analysis," Advances Materials, vol. 18, pp. 3149-3153, (Dec. 4, 2006).
Wang et al., "Electronics and Optoelectronics of Two-Dimensional Transition Metal Dichalcogenides," Nature Nanotechnology, vol. 7, pp. 699-712, (Nov. 6, 2012).
Liu et al., "An Enzyme-Based E-DNA Sensor for Sequence-Specific Detection of Femtomolar DNA Targets," J. Am. Chem. Soc., vol. 130(21), pp. 6820-6825, (2008).
Mirando-Castro et al., "Hairpin-DNA Probe for Enzyme-Amplified Electrochemical Detection of Legionella Pnuemophila," Anal. Chem., vol. 79, pp. 4050-4055, (Jun. 1, 2007).
Shimanovsky et al., "Hiding Data in DNA," International Workshop on Information Hiding, Lecture Notes in Computer Science, pp. 373-386, (Dec. 18, 2012).
Church et al., "Next-Generation Digital Information Storage in DNA," Science, vol. 337(6102), p. 6102, (Sep. 28, 2012).
Fuller et al., "Real-Time Single-Molecule Electronic DNA Sequencing by Synthesis Using Polymer-Tagged Nucleotides on a Nanopore Array," Proceedings of the National Academy of Sciences, vol. 113(19), pp. 5233-523, (May 10, 2016).
Hanief, Topic, Pineda-Vargas, "Solid State Dewetting of Continuous Thin Platinum Coatings," Nuclear Instruments and Methods in Physics Research, vol. 363, pp. 173-176, (2015).
Sholders et al., "Distinct Conformations of a Putative Translocation Element in Poliovirus Polymerase," Journal of Molecular Biology, vol. 426(7), pp. 1407-1419, (Apr. 3, 2014).
USPTO; Requirement for Restriction dated Nov. 2, 2011 in U.S. Appl. No. 12/667,583.
USPTO; Non-Final Office Action dated Sep. 28, 2018 in U.S. Appl. No. 12/667,583.
USPTO; Advisory Action dated Nov. 14, 2018 in U.S. Appl. No. 15/728,400.
USPTO; Non-Final Office Action dated Nov. 30, 2018 in U.S. Appl. No. 15/979,135.
USPTO; Notice of Allowance dated Dec. 6, 2018 in U.S. Appl. No. 15/728,400.
USPTO; Requirement for Restriction dated Dec. 17, 2018 in U.S. Appl. No. 16/015,049.
USPTO; Non-Final Office Action dated Dec. 26, 2018 in U.S. Appl. No. 16/015,028.
USPTO; Non-Final Office Action dated Feb. 1, 2019 in U.S. Appl. No. 16/152,190.
USPTO; Final Office Action dated Feb. 19, 2019 in U.S. Appl. No. 12/667,583.
PCT; International Search Report in Application No. PCT/US2018/048873.
PCT; Written Opinion in Application No. PCT/US2018/048873.
Mastrototaro et al., "Thin-Film Flexible Multielectrode Arrays for Voltage Measurements in the Heart," IEEE Engineering in Medicine & Biology Society 11th Annual International Conference, 1 Page, (1989).
Mastrototaro et al., "Rigid and Flexible Thin-Film Multielectrode Arrays for Transmural Cardiac Recording," IEEE Transactions on Biomedical Engineering, vol. 39, pp. 217-279, (1992).
Van Gerwin et al., "Nanoscaled Interdigitated Electrode Arrays for Biochemical Sensors," Sensors and Actuators B, vol. 49, pp. 73-80, (1998).
Santschi et al., "Interdigitated 50nm Ti Electrode Arrays Fabricated using $XeF_2$ Enhanced Focused Ion Beam Etching," Nanotechnology, vol. 17, pp. 2722-2729, (2006).
Javey et al., "Layer-By-Layer Assembly of Nanowires for Three-Dimensional, Multifunctional Electronics," Nano Letters, vol. 7, pp. 773-777, (2007).
Fan et al., "Detection of MicroRNAs Using Target-Guided Formation of Conducting Polymer Nanowires in Nanogaps," Journal of the American Chemical Society, vol. 129, pp. 5437-5443, (2007).
Kitsara et al., "Single Chip Interdigitated Electrode Capacitive Chemical Sensor Arrays," Sensors and Actuators B, vol. 127, pp. 186-192, (2007).
Xu et al., "Fabrication of Complex Metallic Nanostructures by Nanoskiving," American Chemical Society Nano, vol. 1(3), pp. 215-227, (2007).
Berdat et al., "Label-Free Detection of DNA with Interdigitated Micro-Electrodes in a Fluidic Cell," Lab on a Chip, vol. 8, pp. 302-308, (2008).

(56) References Cited

OTHER PUBLICATIONS

Dickey et al., "Electrically Addressable Parallel Nanowires with 30 NM Spacing from Micromolding and Nanoskiving," Nano Letters, vol. 8(12), pp. 4568-4573, (2008).
Singh et al., "3D Nanogap Interdigitated Electrode Array Biosensors," Analytical and Bioanalytical Chemistry, vol. 397, pp. 1493-1502, (2010).
Bhura, "3D Interdigitated Electrode Array (IDEA) Biosensor for Detection of Serum Biomarker," Master Thesis, Portland State University, 68 Pages, (2011).
Ino et al., "Addressable Electrode Array Device with IDA Electrodes for High-Throughput Detection," Lab on a Chip, vol. 11, p. 385-388, (2011).
Bonilla et al., "Electrical Readout of Protein Microarrays on Regular Glass Slides," Analytical Chemistry, vol. 83, pp. 1726-1731, (2011).
Alm et al., "Electrical Immunosensor Based on a Submicron-Gap Interdigitated Electrode and Gold Enhancement," Biosensors and Bioelectronics, vol. 26, pp. 4690-4696, (2011).
Singh et al., "Evaluation of Nanomaterials-Biomolecule Hybrids for Signals Enhancement of Impedimetric Biosensors," 11th IEEE International Conference on Nanotechnology, pp. 707-710, (2011).
Singh et al., "Nanoparticle-Enhanced Sensitivity of a Nanogap-Interdigitated Electrode Array Impedimetric Biosensor," Langmuir, vol. 27, pp. 13931-13939, (2011).
Chen et al., "Fabrication of Submicron-Gap Electrodes by Silicon Volume Expansion for DNA-Detection," Sensors and Actuators A, vol. 175, pp. 73-77, (2012).
Branagan et al., "Enhanced Mass Transport of Electroactive Species to Annular Nanoband Electrodes Embedded in Nanocapillary Array Membranes," Journal of the American Chemical Society, vol. 134, pp. 8617-8624, (2012).
Ino et al., "Local Redox-Cycling-Based Electrochemical Chip Device with Seep Microwells for Evaluation of Embryoid Bodies," Angewandte Chemie International Edition, vol. 51, pp. 6648-6652, (2012).
Botsialas et al., "A Miniaturized Chemocapacitor System for the Detection of Volatile Organic Compounds," Sensors and Actuators B, Chemical, vol. 177, pp. 776-784, (2013).
Sanguino et al., "Interdigitated Capacitive Immunosensors with PVDF Immobilization Layers," IEEE Sensors Journal, vol. 14(4), pp. 1260-1265, (Apr. 2014).
Van Megan et al., "Submicron Electrode Gaps Fabricated by Gold Electrodeposition at Interdigitated Electrodes," Key Engineering Materials, vol. 605, pp. 107-110, (2014).
MacNaughton et al., "High-Throughput Heterogeneous Integration of Diverse Nanomaterials on a Single Chip for Sensing Applications," PLOS One, vol. 9(10), e111377, 7 Pages, (2014).
Kitsara et al., "Small-Volume Multiparametric Electrochemical Detection at Low Cost Polymeric Devices Featuring Nanoelectrodes," SPIE, vol. 9518, 9 Pages, (2015).
Alayo et al., "Gold Interdigitated Nanoelectrodes as a Sensitive Analytical Tool for Selective Detection of Electroactive Species via Redox Cycling," Microchim Acta, vol. 183, pp. 1633-1639, (2016).
Han et al., "Redox Cycling in Nanopore-Confined Recessed Dual-Ring Electrode Arrays," Journal of Physical Chemistry C, vol. 120, pp. 20634-20641, (2016).
Okinaka et al., ""Polymer" Inclusions in Cobalt-Hardened Electroplated Gold," Journal the of Electrochemical Society, vol. 125, p. 1745, (1978).
Braun et al., "DNA-Templated Assembly and Electrode Attachment of a Conducting Silver Wire," Letters to Nature, vol. 391(6669), pp. 775-778, (Feb. 1998).
Chen et al., "Electrochemical Approach for Fabricating Nanogap Electrodes with Well Controllable Separation," Applied Physics Letters, vol. 86, pp. 123105.1-123105.3, (2005).
Hashioka et al., "Deoxyribonucleic Acid Sensing Device with 40-NM-Gap-Electrodes Fabricated by Low-Cost Conventional Techniques," Applied Physics Letters, vol. 85(4), p. 687-688, (Jul. 2004).
He et al., "Electromechanical Fabrication of Atomically Thin Metallic Wires and Electrodes Separated with Molecular-Scale Gaps," Journal of Electroanalytical Chemistry, vol. 522, pp. 167-172, (Jan. 2002).
Hwang et al., "Electrical Transport Through 60 Base Pairs of Poly (dG)-Poly (dC) DNA Molecules," Applied Physics Letters, vol. 81(6), p. 1134-1136, (Aug. 2002).
Iqbal et al., "Direct Current Electrical Characterization of ds-DNA in Nanogap Junctions," Applied Physics Letter, vol. 86, p. 153901-1-153901-3, (Apr. 2005).
Liu et al., "Controllable Nanogap Fabrication on Microchip by Chronopotentiometry," Electrochimica Acta, vol. 50, pp. 3041-3047, (2005).
Qing et al., "Finely Tuning Metallic Nanogap Size with Electrodeposition by Utilizing High-Frequency Impedance in Feedback," Angewandte Chemie Int ed, vol. 44, pp. 7771-7775, (2005).
Reichert et al., "Driving Current Through Single Organic Molecules," Physical Review Letters, vol. 88(17), pp. 176804-1-176804-4, (Apr. 2002).
Reed et al., "Conductance of a Molecular Junction Reports," Science, vol. 278, pp. 252-254, (Oct. 1997).
Roppert et al., "A New Approach for an Interdigitated Electrodes DNA-Sensor," XVIIIth International Symposium on Bioelectrochemistry and Bioenergetics, Bioelectrochemistry, p. 143, (2005).
Kraft, "Doped Diamond: A Compact Review on a New, Versatile Electrode Material," International Journal of Electrochemistry, vol. 2, pp. 355-385, (May 2007).
USPTO; Advisory Action dated May 22, 2019 in U.S. Appl. No. 15/979,135.
USPTO; Restriction Requirement dated May 29, 2019 in U.S. Appl. No. 16/250,929.
USPTO; Notice of Allowance dated May 30, 2019, in U.S. Appl. No. 16/152,190.
USPTO; Non-Final Office Action dated Jun. 25, 2019 in U.S. Appl. No. 15/979,135.
USPTO; Final Office Action dated Jun. 19, 2019 in U.S. Appl. No. 16/015,049.
USPTO; Final Office Action dated Jul. 10, 2019 in U.S. Appl. No. 15/050,270.
PCT; International Search Report and Written Opinion dated Jan. 18, 2019 in Application No. PCT/US2018/055264.
EP; European Search Report dated Jan. 30, 2019 in Application No. EP16815467.2.
Briglin et al., "Exploitation of Spatiotemporal Information and Geometric Optimization of Signal/Noise Performance Using Arrays of Carbon Black-Polymer Composite Vapor Detectors," Sensors and Actuators B, vol. 82, pp. 54-74, (2002).
Cosofret et al., "Microfabricated Sensor Arrays Sensitive to pH and K+ for Ionic Distribution Measurements in the Beating Heart," Analytical Chemistry, vol. 67, pp. 1647-1653, (1995).
Henry et al., "Microcavities Containing Individually Addressable Recessed Microdisk and Tubular Nanoband Electrodes," Journal of the Electrochemical Society, vol. 146(9), pp. 3367-3373, (1999).
Lin et al., "An Addressable Microelectrode Array for Electrichemical Detection," Analytical Chemistry, vol. 80, pp. 6830-6833, (2008).
Thompson, "Solid-State Dewetting of Thin Films," Department of Materials Science and Engineering, vol. 42, pp. 399-434, (2012).
USPTO; Advisory Action dated Sep. 4, 2018 in U.S. Appl. No. 15/796,080.
USPTO; Non-Final Office Action dated Sep. 4, 2018 in U.S. Appl. No. 15/979,135.
USPTO; Notice of Allowance dated Sep. 12, 2018 in U.S. Appl. No. 15/728,412.
USPTO; Advisory Action dated Sep. 26, 2018 in U.S. Appl. No. 15/050,270.
USPTO; Notice of Allowance dated Oct. 11, 2018 in U.S. Appl. No. 15/796,080.
USPTO; Advisory Action dated Oct. 12, 2018 in U.S. Appl. No. 15/728,400.
USPTO; Requirement for Restriction dated Oct. 15, 2018 in U.S. Appl. No. 16/015,028.

(56) References Cited

OTHER PUBLICATIONS

PCT; International Preliminary Report on Patentability in Application No. PCT/US2017/017231.
USPTO; Non-Final Office Action dated Jul. 30, 2019 in the U.S. Appl. No. 16/015,028.
USPTO; Non-Final Office Action dated Aug. 22, 2019 in the U.S. Appl. No. 16/011,065.
USPTO; Restriction Requirement dated Sep. 19, 2019 in U.S. Appl. No. 16/073,706.
USPTO; Non-Final Office Action dated Aug. 19, 2019 in U.S. Appl. No. 12/667,583.
CN; Notice of the First Office Action dated Sep. 2, 2019 in Chinese Application No. 201680049272.8.
EP; European Search Report dated Aug. 2, 2019 in Application No. EP16885434.7.
EP; European Search Report dated Aug. 2, 2019 in Application No. EP17745026.9.
USPTO; Notice of Allowance dated Oct. 23, 2019 in U.S. Appl. No. 16/250,929.
USPTO; Non-Final Office Action dated Oct. 24, 2019 in U.S. Appl. No. 16/073,706.
USPTO; Notice of Allowance dated Nov. 8, 2019 in U.S. Appl. No. 16/015,028.
USPTO; Non-Final Office Action dated Nov. 5, 2019 in U.S. Appl. No. 16/015,049.
USPTO; Notice of Allowance dated Dec. 11, 2019 in U.S. Appl. No. 15/979,135.
USPTO; Notice of Allowance dated Jan. 6, 2020 in U.S. Appl. No. 15/050,270.
EP; European Search Report dated Oct. 24, 2019 in Application No. 17757146.
USPTO; Final Office Action dated Mar. 6, 2020 in U.S. Appl. No. 16/011,065.
USPTO; Notice of Allowance dated Feb. 20, 2020 in U.S. Appl. No. 16/015,049.
USPTO; Non-Final Office Action dated Apr. 13, 2020 in U.S. Appl. No. 16/070,133.
USPTO; Restriction Requirement dated Apr. 8, 2020 in U.S. Appl. No. 16/479,257.
EP; European Search Report dated Jan. 29, 2020 in Application No. 17745013.7.
EP; European Search Report dated Jan. 29, 2020 in Application No. 17750776.1.
EP; European Search Report dated Feb. 7, 2020 in Application No. 17837566.3.
EP; European Search Report dated Mar. 6, 2020 in Application No. 17835231.6.
Cerofolini et al., "A Hybrid Approach to Nanoelectronics: A Hybrid Approach to Nanoelectrics," Nanotechnology, Institute of Physics Publishing, GB, vol. 16, No. 8, pp. 1040-1047 (2005).
Guo et al., "Conductivity of a single DNA duplex bridging a carbon nanotube gap," Nat. Nanotechnol., vol. 3, No. 3, pp. 1-12 (2008).
Kumar et al., "Terminal Phosphate Labeled Nucleotides: Synthesis, Applications and Linker Effect on Incorporation by DNA Polymerases," Nucleosides, Nucleotides and Nucleic Acids, Taylor and Francis, vol. 24, No. 5-7, pp. 401-408 (2005).
Pugliese et al., "Processive Incorporation of Deoxynucleoside Triphosphate Analogs by Single-Molecule DNA Polymerase I (Klenow Fragment) Nanocircuits," Journal of the American Chemical Society, vol. 137, No. 30, pp. 9587-9594 (2015).
Zafarani et al., "Electrochemical Redox Cycling in a New Nanogap Sensor: Design and Simulation," Journal of Electroanalytical Chemistry, vol. 760, pp. 42-47, (2015).

* cited by examiner

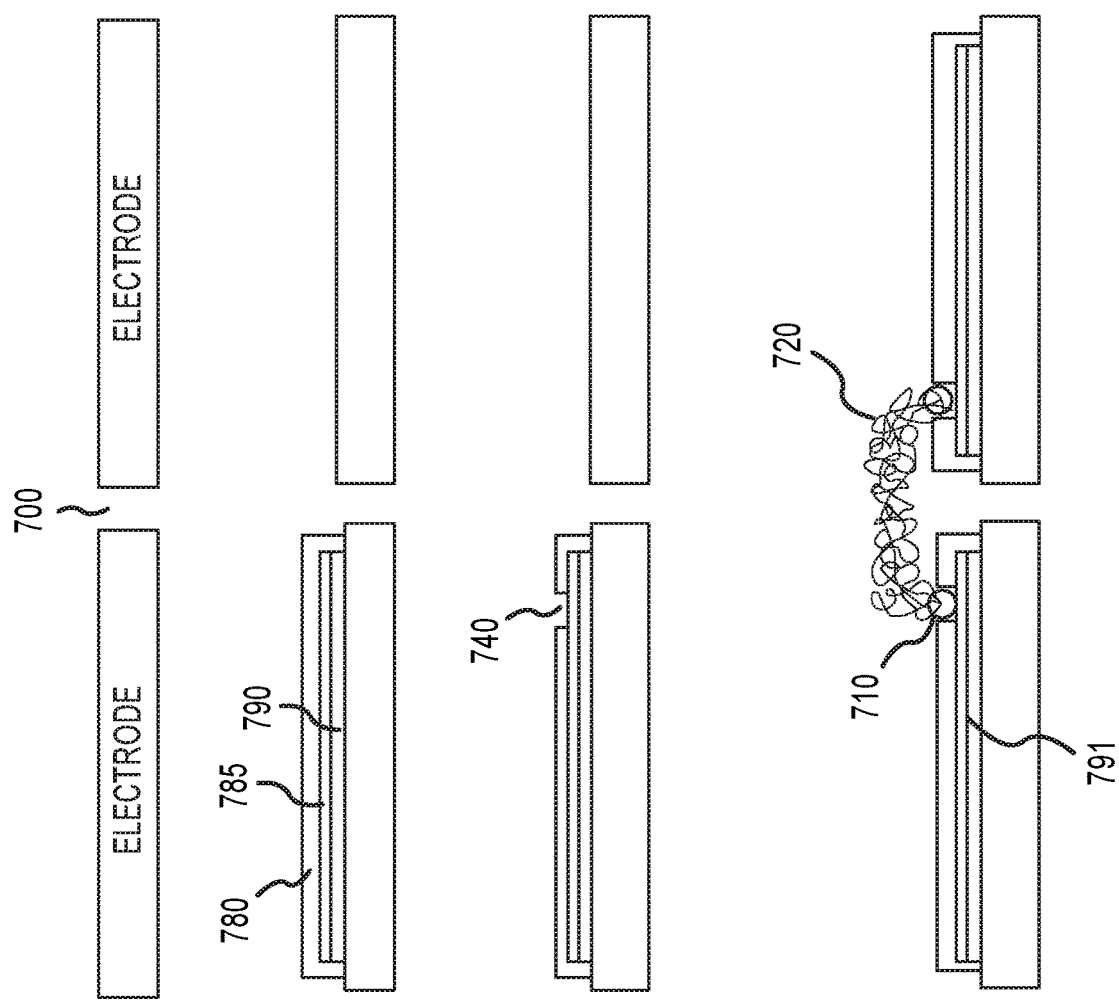

ELECTRONIC LABEL-FREE DNA AND GENOME SEQUENCING

CROSS-REFERENCE TO RELATED APPLICATIONS

This application is a U.S. national phase filing under 35 U.S.C. § 371 of PCT/US2017/017231 filed on Feb. 9, 2017, which claims priority to U.S. Provisional Patent Application No. 62/293,239 filed on Feb. 9, 2016, entitled "ELECTRONIC, LABEL-FREE DNA AND GENOME SEQUENCING APPARATUS, METHOD OF FABRICATION, AND APPLICATIONS THEREOF," the disclosures of which are incorporated herein by reference.

FIELD

This disclosure relates generally to nanotechnology, nanofabrication and nanoelectronics, and more particularly to systems, devices, and processes for electronic sensing and analyzing of individual biomolecules, including DNA and proteins.

BACKGROUND

Since the discovery of DNA, there has been a concerted effort to develop ways to actually experimentally determine the sequences of the constitutive chemical bases. The first method for systematically sequencing DNA was introduced by Sanger in 1978.

This basic method was automated in a commercial instrument platform in the late 1980's, enabling the sequencing of the first human genome. The success of this effort motivated the development of a number of "massively parallel" sequencing platforms, with the goal of dramatically reducing the cost and time required to sequence a human genome. These automated methods generally rely on processing millions to billions of sequencing reactions at the same time, in highly miniaturized microfluidic formats.

Although a variety of other related techniques and commercial platforms followed, further improvements in quality and accuracy of sequencing, as well as reductions in cost and time, remain highly desirable. This is especially true to make genome sequencing practical for widespread use in precision medicine, where it is desirable to sequence the genomes of millions of individuals with a clinical grade of quality. Further, many DNA sequencing techniques utilize optical means with fluorescence reporters. Such methods can be cumbersome, slow in detection speed, and difficult to mass produce or make affordable. Label-free DNA or genome sequencing approaches would have the advantages of not having to use fluorescent type labeling processes and associated optical systems, and are thus particularly needed.

SUMMARY

This invention discloses new, manufacturable and highly-scalable techniques of sub-10 nm nano-electrode design and fabrication, which comprise parts of label-free DNA or genome sequencing methods, apparatus, and applications.

This invention provides unique structures, compositions and means of manufacturing the same, for extremely small and high-density nano-electrode arrays for use in electronic DNA sequencing systems. Such nano-electrode systems may also be used in analyzing other types of biomolecules, such as proteins, depending on how the nano-electrodes are functionalized to interact with biomolecule sensing targets.

In general, the nano-electrode systems disclosed herein may comprise part of a system for such biomolecule analysis, wherein the nano-electrode system is coupled to biomolecules to constitute a molecular electronics sensor with specific application to sensing and characterizing a biomolecule target, in particular applications to sequencing of a DNA molecule, or a collection of such molecules constituting an entire genome.

In various aspects of the present disclosure, a method of manufacturing a device for DNA or genome sequencing is disclosed. The method includes: disposing a pair of electrodes on a substrate with the electrodes separated by a nanogap; depositing a resist layer over the pair of electrodes; patterning the resist layer to create an exposed region on each electrode at or near the nanogap; exposing the electrodes to plasma etching or gold (Au) ion beam implantation to roughen the surface within each exposed region; and exposing the exposed regions to a biomolecule, wherein the biomolecule has at least first and second ends, with each end including a functionalization for bonding to the pair of electrodes, wherein the biomolecule bridges the nanogap, with the first and second ends of the biomolecule being bound to the exposed regions.

In certain aspects, the resist layer may be an electrically insulating polymer or an oxide coating measuring from about 3 nm to about 20 nm in thickness, and the electrodes may be gold (Au) electrodes. In some examples, the patterning used is e-beam or nano-lithography.

In various embodiments, plasma etching includes RF plasma, DC plasma or sputter etching processes. The plasma etching or the Au ion beam implantation step results in an increase in the surface area of the electrode within each exposed region by at least 50% from the surface area of the exposed region prior to plasma etching or Au ion beam implantation.

In various embodiments of the present invention, a method of manufacturing a device for DNA or genome sequencing is disclosed. The method includes: disposing a pair of electrodes on a substrate, with the electrodes separated by a nanogap; depositing a resist layer over the pair of electrodes; patterning the resist layer to create an exposed region on each electrode at or near the nanogap; exposing the electrodes to Au nanoparticles, wherein the Au nanoparticles attach to the electrode surfaces within each exposed region; annealing the array at from about 200° to about 500° C. to bond the Au nanoparticles to the electrode surface; and exposing the exposed regions to a biomolecule, wherein the biomolecule has at least first and second ends, with each end including a functionalization for bonding to the pair of electrodes, wherein each biomolecule bridges the nanogap, with the first and second ends of the biomolecule being bound to the exposed regions. In certain examples, the resist layer is an electrically insulating ceramic layer such as $Al_2O_3$ or $SiO_2$ and the electrodes are gold (Au). The patterning step may include e-beam or nano-lithography.

In various embodiments of the present disclosure, a method of manufacturing a device for DNA or genome sequencing is disclosed. The method includes: disposing a pair of Au metal alloy electrodes on a substrate with the electrodes separated by a nanogap; depositing a resist layer over the electrode pair; patterning the resist layer to create an exposed region on each electrode at or near the nanogap; exposing the electrodes to an etchant solution to selectively remove the non-Au metal from the alloy within each exposed region; and exposing the exposed regions to a biomolecule, wherein the biomolecule has at least first and second ends, with each end including a functionalization for bonding to the pair of electrodes, wherein each biomolecule bridges the nanogap, with the first and second ends of the biomolecule being bound to the exposed regions. The Au metal alloy may be selected from the group consisting of Au—Si, Au—Ge, Au—Bi, Au—Co, Au—Mo, Au—Rh, Au—Ru, and Au—W. In certain aspects, the resist layer is an electrically insulating ceramic layer such as $Al_2O_3$ or $SiO_2$.

In certain examples, the method may further include a step of annealing at from about 200° to about 600° C. for about 10 minutes to about 12 hours to promote phase separation between the Au and non-Au metal.

In various embodiments of the present disclosure, a method of manufacturing a device for DNA or genome sequencing is disclosed. The method includes: disposing a pair of electrodes on a substrate, the electrodes separated by a nanogap; depositing a resist layer over the electrode pair; patterning the resist layer to create an exposed region on each electrode at or near the nanogap; depositing Au—Ag or Au—Cu alloy onto the electrode surface within each exposed region; exposing the electrodes to an etchant solution to selectively remove the non-Au metal from the alloy deposited within each exposed region; and exposing the exposed regions to a biomolecule, wherein the biomolecule has at least first and second ends, with each end including a functionalization for bonding to the pair of electrodes, wherein each biomolecule bridges the nanogap, with the first and second ends of the biomolecule being bound to the exposed regions. In certain examples, the resist layer is an electrically insulating ceramic layer such as $Al_2O_3$ or $SiO_2$. Also, the electrodes can be gold (Au) electrodes. In various examples, the patterning process includes e-beam or nano-lithography.

In various embodiments of the present disclosure, a method of manufacturing a device for DNA or genome sequencing is disclosed. The method includes: disposing a pair of electrodes on a substrate, the electrodes separated by a nanogap; depositing a latchable magnetic layer over the electrodes; depositing a resist layer over the latchable magnetic layer; patterning the resist layer to create an exposed region at or near the nanogap in which the latchable magnetic layer is exposed; exposing the electrodes to an external magnetic field or to an applied voltage to magnetize the latchable magnetic layer; and exposing the exposed regions to a biomolecule, wherein the biomolecule has at least first and second ends with each end tagged with a magnetic nanoparticle for attraction to the magnetized latchable magnetic layer, wherein the biomolecule bridges the nanogap, with each magnetic nanoparticle held to each electrode at the exposed regions. In certain examples, the latchable magnetic layer is a FeCrCo or FeCuNi spinodal alloy with Hc higher than 10 Oe. This method may further include a step of depositing a layer of Au over the latchable magnetic layer prior to the step of patterning the resist layer. Further, the magnetic layer can be magnetized or demagnetized to enable magnetically attracted attachment of magnetic nanoparticle-tagged biomolecules or removal and cleaning-out of attached magnetic nanoparticle-tagged biomolecules with a permanent magnet sweep, allowing multiple repeat operations of the device.

In various embodiments of the present disclosure, a method of manufacturing a device for DNA or genome sequencing is disclosed. The method includes: disposing a pair of platinum (Pt) or rhenium (Rh) electrodes on a substrate, the electrodes separated by a nanogap; depositing a gold (Au) film measuring from about 1 nm to about 10 nm in thickness over the electrode pair; patterning the resist layer to create an exposed region on each electrode at or near the nanogap; annealing the electrodes to induce spheroidization of the Au film into Au spheres, with one sphere disposed within each exposed region; etching the spheres to reduce the height of the spheres; repeating the annealing and etching steps at least two more times; and exposing the Au spheres to a biomolecule, wherein the biomolecule has at least first and second ends, with each end including a functionalization for bonding to the Au spheres, wherein the biomolecule bridges the nanogap, with the first and second ends of the biomolecule being bound to the Au spheres. In this method, the annealing can be from about 200° to about 400° C. for about 10 minutes to about 12 hours, or the time/temperature sufficient to cause spheroidization. The etching step may include at least one of ion milling, sputter etching, and masking and chemical dissolution.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the drawing figures.

FIG. 7(b) illustrates magnetic attraction for secure adhesion of biomolecule. The magnetic layer is deposited on Pt, Pd, or Rh type electrode surface;

It is to be understood that the drawings are for purposes of illustrating the concepts of the invention and are not to scale.

DETAILED DESCRIPTION

The detailed description of embodiments herein makes reference to the accompanying drawings, which show particular embodiments by way of illustration. While these embodiments are described in sufficient detail to enable those skilled in the art to practice the invention, it should be understood that other embodiments may be realized and that logical, chemical, and mechanical changes may be made without departing from the spirit and scope of the inventions. Thus, the detailed description herein is presented for purposes of illustration and not as a source of limitation. For example, unless otherwise noted, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

Definitions

Any term not expressly defined should be given the common meaning known to a person skilled in the art.

As used herein, the term "sub-10 nm" refers to the size of devices and components therein, and the scale at which methods can be executed. In particular, the term refers to physical structures measuring less than about 10 nm in size, and the ability to manipulate steps in various processes on a scale of less than about 10 nm.

As used herein, the term "nanogap" refers to a space, or "gap," between elements, such as between two electrodes or two conductive islands, measuring in the nanometer range. Similarly, the term "nanogapped" refers to two elements having a gap between them on a nanometer scale.

As used herein, the term "label-free" refers to a process that does not require fluorescence labeling, or is in other words, is "fluorescence-free."

As used herein, symbols for atomic elements and the associated names of the elements may be used interchangeably, or together. For example, the element gold may be denoted herein "Au," "gold," or "gold (Au)."

As used herein, the term "latchable magnetic stripe" (or "latchable magnetic layer") refers to a thin film or layer of magnetizable material having a capability to change magnetization direction in response to an external magnetic field, such as a layer having magnetic properties that are programmable and reconfigurable as an applied field or an applied voltage is altered.

Figure 1:
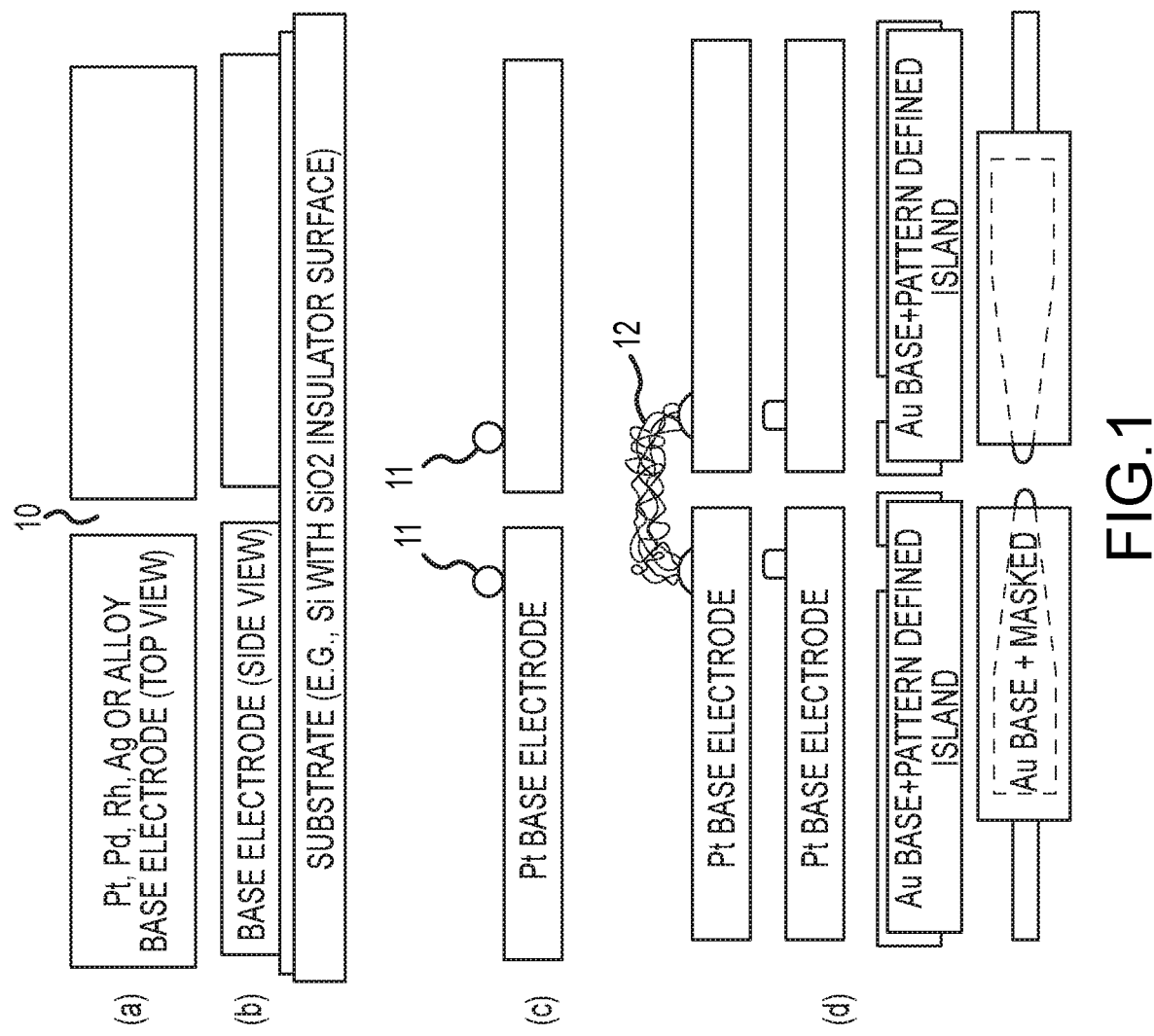
FIG. 1 illustrates genome sequencing compatible electrodes having a structure comprising a 5-20 nm nanogap, with a pair of Au islands for attaching or immobilizing biomolecules such as proteins or fragmented DNA for the purpose of fluorescence-free (label-free) detection of nucleotide attachments via electrical measurements.

DNA or genome sequencing by electronic conductance measurements often entails using devices comprising a pair of electrically separated, conductive islands onto which a biomolecule is bridged, and through which electronic current or voltage signals are detected. Referring to the drawings, FIG. 1 illustrates electrodes having a 5-20 nm nanogap and a pair of gold (Au) islands for attaching or otherwise immobilizing biomolecules such as proteins or fragmented DNA for use in devices capable of label-free detection of nucleotide attachments via electronic conductance measurements. FIG. 1(a) shows a top view, and FIG. 1(b) shows a side view, of an embodiment of a nanogapped electrode pair usable for genome/DNA sequencing by electronic conductance measurements. The electrodes may comprise a stable and inert metal having high conductivity. The nanogap 10 between the electrodes may be from about 5-20 nm in width. Exemplary electrode metals include, but are not limited to, platinum (Pt), palladium (Pd), rhenium (Rh), titanium (Ti), silver (Ag), and gold (Au), or their alloys, with gold (Au) being the most widely used electrode material. However, in accordance to various embodiments of the present disclosure, alternatives to Au, such Pt, Pd, Rh and their alloys, can be utilized so as to prevent the non-specific, random attachment of biomolecules, proteins or DNAs on the electrode surface. For example, by using Pt base electrodes, biomolecules are much less prone to attach directly on the Pt surface. Thus, with an addition of pair of Au islands measuring several nanometers in size on to the Pt, the attachment of a biomolecule, especially a single biomolecule, can be confined to the gold islands rather than on the Pt electrode surface itself.

Nanoscale particles, such as, for example, ~5 nm diameter gold nanoparticles, are difficult to accurately position and place directly on an electrode surface, such as on to a Pt electrode. In certain instances, Atomic Force Microscopy (AFM) or Scanning Probe Microscopy (SPM) methods may be used to pick-up, move, and release an individual Au nanoparticle onto an electrode surface, whereby van der Walls forces assist in holding the nanoparticle at its intended location, such as illustrated in FIG. 1(c), depicting Au nanoparticles 11 sitting indiscriminately on top of the Pt base electrodes, (see, for e.g., Huang, et al., U.S. Patent Application Publication No. 2014/0048776, published on Feb. 20, 2014). However, such delicate movement and placement of nanoparticles can lead to nanoparticles that are not particularly well adhered onto the electrode surface. Further, the positioning of individual nanoparticles at desired locations is not reproducible. These nanoparticles 11, which are not-so-strongly adhered, as illustrated in FIG. 1(c), will cause high contact resistance and reduced electrical conductivity. Further, these Au nanoparticles can be easily moved laterally to a different location, or detached entirely during handling, for example, during washing or microfluidic processing of biomolecules. Accordingly, such AFM guided placement of a nanoparticle, one by one, is laborious, time consuming and not scalable for low-cost manufacturing.

Therefore, in accordance with an embodiment of the present disclosure, the Au nanoparticle is more strongly bonded onto the electrode surface such that the contact area of the Au particle used in the bonding with the electrode surface comprises at least 20%, at least 30%, at least 40%, at least 50%, at least 60%, at least 70%, preferably at least 80%, more preferably at least 90%, and even more preferably up to 100% of the Au particle diameter, as illustrated in the top example in FIG. 1(d), which shows hemispherically shaped islands. In this example of hemispherical islands, a single biomolecule 12 is shown in contact with the islands and bridging the gap between the electrodes. The second example in FIG. 1(d) illustrates an embodiment comprising "pillar" shaped islands on the Pt base electrodes, which are available for bonding with a biomolecule bridge.

Another embodiment according to the disclosure avoids fabricating Au islands on Pt electrodes entirely, relying instead on exposed portions of Au electrodes for biomolecule bonding and bridging. As illustrated in the third example in FIG. 1(d), a nano-patterned mask is used to block almost the entire Au electrode surface except for a selected region left exposed and available for selective biomolecule attachment. In a variation of this concept, a resist layer, such as for example, PMMA (polymethylmethacrylate), methacrylate-based co-polymers, hydrogen silsesquioxane (HSQ), and various siloxane polymers, can be utilized to cover the majority of the Au electrodes except for just the tips of the electrodes, as illustrated in the fourth example of FIG. 1(d). These two methods that utilize a resist layer are discussed in more detail herein.

Figure 2:
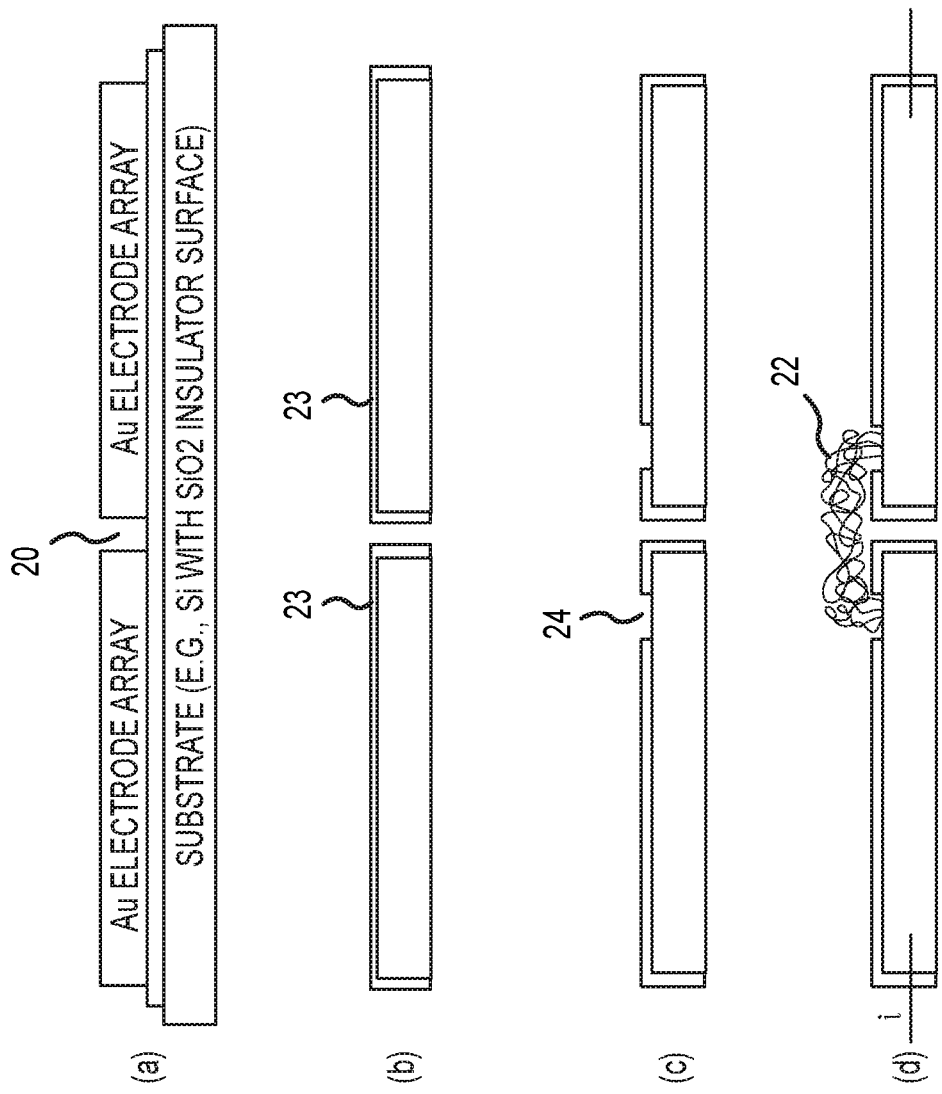
FIG. 2 illustrates an embodiment of nano-patterning usable to obtain local-area-defined, massively parallel, Au island electrode arrays.

FIG. 2 illustrates an embodiment of a nano-patterning process usable to obtain local-area defined electrodes having exposed regions on Au electrodes and single biomolecule bonding and bridging. The process begins with a pair of Au electrodes as illustrated in FIG. 2(a). This cross-sectional side view illustration shows two Au electrodes as a pair of electrodes on a substrate comprising Si with a $SiO_2$ insulator surface. The nanogap 20 in each electrode pair is from about 5 nm to about 20 nm. The electrodes are labeled "array" to emphasize that in a device, there can be a plurality of such electrode pairs, from less than a hundred, to hundreds, or thousands, or millions or more electrode pairs. The goal of the process illustrated in FIG. 2 is to obtain a single nano-defined exposed region on each Au electrode, measuring about 3-10 nm in diameter, which will allow bonding of only one end of one biomolecule in each exposed region. In other words, the exposed region on each electrode needs to be sub-10 nm. For this purpose, and as illustrated in FIG. 2(b), a positive or negative resist layer 23 is added over the electrode pair. A positive resist (e.g., polymethylmethacrylate (PMMA)), or a negative resist, (e.g., hydrogen silsesquioxane (HSQ) or SU-8 epoxy resist), can be used, and any of these are compatible with subsequent e-beam or nano-imprint lithography. In certain examples, the resist layer 23 comprises a negative resist. The e-beam or nano-imprint lithography is then used to pattern the exposed regions 24 as illustrated in FIG. 2(c).

In alternative embodiments, $Al_2O_3$, $SiO_2$ or $Si_3N_4$, or other oxide or nitride layers, may be deposited on the Au electrodes and used as an insulating layer instead of using a polymer resist layer. In this case, a very thin adhesion layer, such as a 1-3 nm thick Ti layer, may be deposited on the Au electrode surface before the oxide or nitride coating is applied. This protective coating, whether polymeric or ceramic, serves as an electrical insulator and also as a coating that prevents or minimizes the adhesion of biomolecules at unwanted locations.

Referring to FIG. 2(c), the configuration of an exposed region 24 may be any shape, such as circular, oval, square, rectangular, or any other geometry. The size of each exposed region 24 on an Au electrode is about 3 nm to about 15 nm in diameter on average (or the equivalent dimension across and parallel to the electrode surface if not circular in shape). In certain embodiments, each exposed region 24 is about 5 nm to about 10 nm in diameter (or equivalent dimension across the region if not circular).

The process depicted sequentially in FIG. 2 is amenable to the processing of massively parallel array sequencing devices. Nano-patterning approaches such as nano-imprinting, electron beam lithography, shadow mask patterning, EUV (extreme UV) lithography, x-ray lithography, and other known patterning methods, allow fabrication of at least 1,000, preferably at least 10,000 or more, single electrode pair devices simultaneously. Such a large array of electrodes in a sequencing device greatly speeds up sequencing speed and reduces sequencing cost. FIG. 2(d) illustrates an attached biomolecule 22 (e.g., a protein, a DNA segment, etc.) attached at each of its ends to the exposed region on each electrode to form a bridge. In various embodiments, the biomolecule 22 may be immobilized into the position shown by functionalized ends using antibody-antigen, biotin-streptavidin, peptide bonding, functionalized ligands, surface charges, or other biomolecule immobilizing techniques. A complete electrode pair device illustrated in FIG. 2(d) is shown comprising electrical connections from each electrode, used for electrical interrogation ("i") of sequencing events that comprise interactions of the biomolecule 22 with other molecules.

For molecular electronics devices, including those for protein analysis or DNA/genome sequencing, parallel electronic sensing using an array of many electrode pair devices is desirable. In order to package more electrical measurement devices and circuits within a given space, the electrode dimensions must be reduced to micro- or nano-dimensions. An array of nano-electrodes having the geometry such as shown in FIG. 2 can be utilized. Such an array can be made by using convenient and scalable processing methods such as nano-imprint lithography. Alternative methods such as e-beam lithography, self-assembly and other means may also be utilized.

In DNA and genome sequencing comprising label-free electronic detection, as well as molecular electronics devices in general, a strong and reliable biomolecule-to-electrode (or biomolecule-to-conductive island) attachment is essential, so as to obtain reproducibly strong, noise-reduced signals during electronic interrogation of nucleotide interaction with the biomolecule. Attachment of a biomolecule to a surface can be enhanced if the surface is "roughened," meaning that the surface is modified in a way that increases the surface area onto which the biomolecule is to attach. Ordinarily it is difficult to make branched or porous structures on what are already nano-dimensioned (e.g., 5-10 nm area) structures. However, in accordance with the present disclosure, this difficulty has been overcome, whereby further subdivided nanostructures for enhanced adhesion of biomolecules onto the electrode surface has been accomplished. An embodiment comprising subdivided nanostructures on an electrode surface is where an Au pillar, deposited on an electrode surface, is surface damaged in a way to make at least the top surface rough or porous.

Au surfaces allow for the opportunity to use thiol (—SH) groups on a biomolecule for adhesion (immobilization) of the biomolecule to the Au surface, through Au-sulfur bonding. Nonetheless, if biomolecule adhesion can be enhanced beyond the basic Au-sulfur bonding afforded by thiol groups, the reliability and signal-to-noise ratio in electronic, label-free sequencing can be significantly improved. According to the present disclosure, increasing the surface area of a nano-island of Au increases biomolecule binding to the Au. Herein, further surface nano-structuring of a sub-10 nm island of Au is disclosed.

Figure 3:
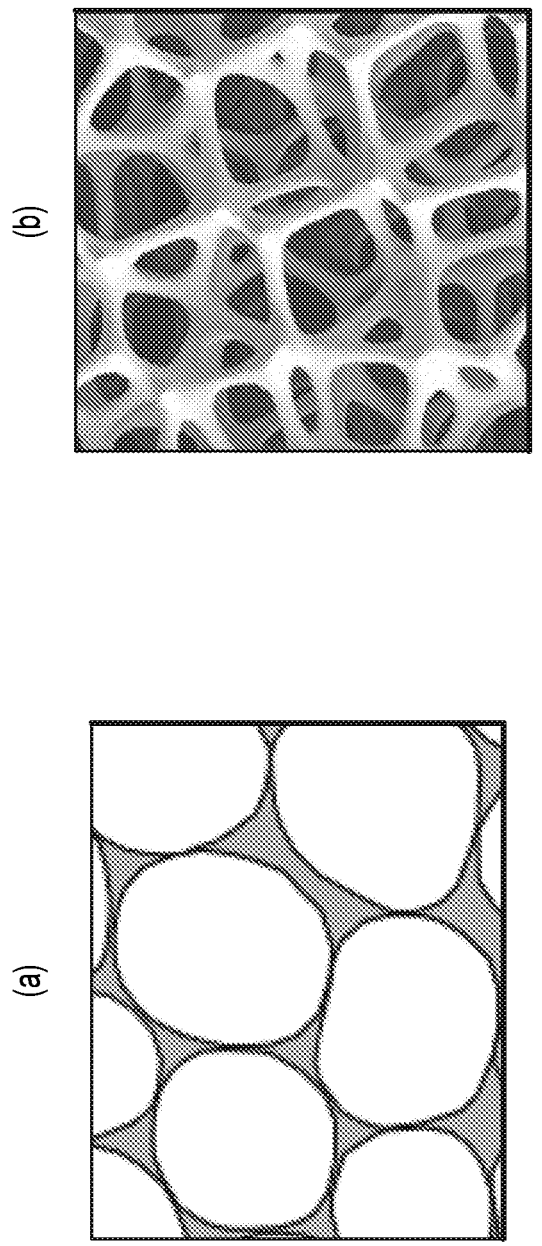
FIG. 3 is a schematic illustration of microstructures having high surface area Au islands, introduced through particle-induced porous structure or etch-induced porous structure methods.

Referring now to FIG. 3, a schematic illustration of exemplary microstructures having large-surface-area Au islands is provided. In accordance with the disclosure, the increase in surface area can be the result of a particle-induced porous structure (illustrated in FIG. 3(a)) or an etch-induced porous structure (illustrated in FIG. 3(b)), or from other means. Methods to produce a particle-induced porous structure and an etch-induced porous structure are detailed herein. According to certain embodiments, the increase in the surface area at or near the top surfaces of Au islands where biomolecules are to be adhered is at least 50%, and preferably at least 100% over a flat surfaced Au islands. The biomolecule adhesion strength is improved by at least 30%, and preferably by at least 60% over adhesion on to plain, unmodified Au islands.

Figure 4:
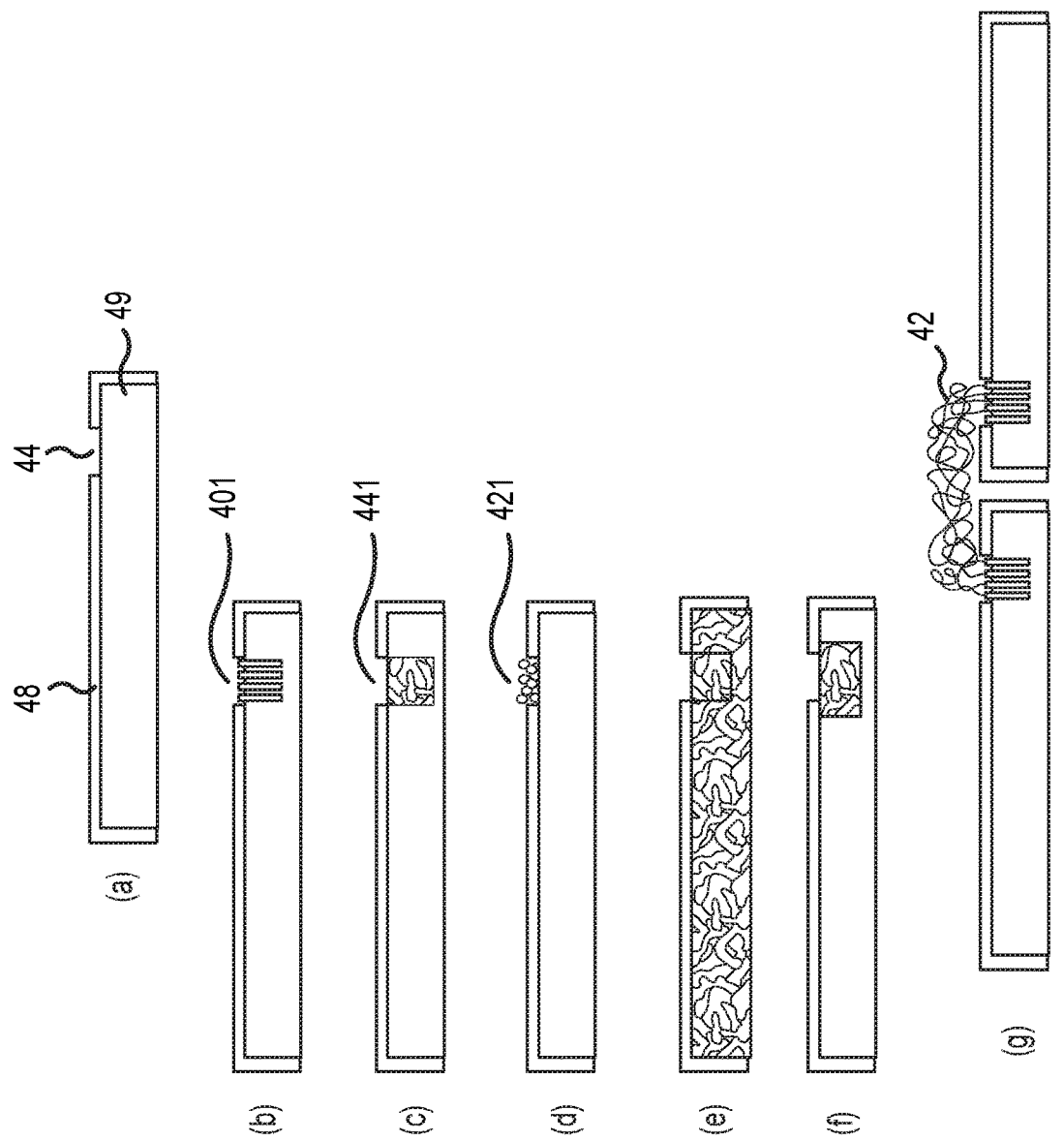
FIG. 4 illustrates a high surface area Au island for stronger, reduced-error enhanced biomolecule adhesion.

Referring now to FIG. 4, exemplary large surface area Au island structures and methods of producing them are shown. As mentioned, increased surface area for bonding biomolecules results in stronger, reproducible, enhanced biomolecule adhesion. In FIGS. 4(a) through 4(f), only the left side each electrode pair is illustrated for the purposes of clarity. FIG. 4(a) schematically illustrates an embodiment of a base electrode structure, comprising electrode 49 and resist layer 48, on which an exposed island location 44. It is inside this region 44 where the surface area of the island is to be increased. The process begins by forming a pattern-defined Au island region on a conductive electrode (e.g., Au, Pd, Pt, Rh, Ag or their alloys) surface, by utilizing insulating coating 48 such as PMMA and other polymers, or an oxide layer such as sputter-deposited $SiO_2$ or $Al_2O_3$. As discussed, e-beam or nano-lithography can be used to create each of the exposed regions 44 on the electrodes. The nature of the coating is chosen based on desirable electrical insulation properties and the resistance the coating has to biomolecule adhesion.

Once the resist layer 48 is patterned, the exposed regions 44 are processed to increase the surface area within the exposed region 44. FIG. 4(b) is an example of a porous surface structure 401 created by plasma etching. In certain embodiments, rough surface structure, such as a porous or vertical nanowire forest type surface structure, can be formed by RF plasma or DC plasma etching (or sputter etching) processing, more selectively on the exposed Au island region. The intensity and duration of plasma etching can be adjusted so as to minimize complete plasma etching of the insulation mask layer material. The thickness of the resist layer may be from about 3 nm to about 20 nm, and this thickness can be adjusted to mitigate complete plasma etching of the mask layer.

A rough surface having an increased surface area can also be created by ion implantation, e.g., by using an Au ion beam. An example of a rough surface formed by ion beam implantation is illustrated as surface 441 in FIG. 4(c). However, ion implantation damage can occur on the Au electrode base underneath the insulating coating, depending on the penetration depth of ions as dictated by the accelerating field and total dose of ion implantation. As such, the insulating resist coating does not necessarily protect the Au surface beneath from ion implantation. However, a resultant roughened surface in areas other than the exposed island region does not affect the sequencing operation because the insulation layer remains covering the roughened electrode surface. In various embodiments of the present disclosure, a post-annealing step may follow the ion implantation.

Another embodiment used to increase the surface area of an Au island comprises attaching Au nanoparticles 421 to the exposed Au region, as shown in FIG. 4(d). Au nanoparticles attached to the Au electrode increases the surface area which results in enhanced biomolecule attachment. In various examples, Au nanoparticles measuring about 1 nm to about 2 nm in diameter, made by known methods, tend to preferentially attach naturally to the Au electrode within the exposed region. The Au nanoparticles thus deposited may then be optionally annealed at from about 200 to about 500° C. Higher temperatures can only be used if the insulating layer 48 is ceramic based, (e.g., if the insulating layer comprises $Al_2O_3$ or $SiO_2$). Post-annealing at these temperatures improves the adherence of the Au nanoparticles to the exposed Au surface. An example of particle-induced porous structure is illustrated, for example, in FIG. 3(a).

FIG. 4(e) represents another embodiment of a process to increase the surface area of an exposed Au island surface, leveraging the immiscibility that Au and Fe exhibit at or near room temperature. For this process, an electrode base layer may be made, for example, from an Au—Fe alloy having about 50 wt. % Au and 50 wt. % Fe by sputtering or evaporation deposition. Toward room temperature, the alloy phase segregates into an Au matrix embedded with Fe nanoparticles that have precipitated out. The Fe nanoparticles can then be etched away to leave behind a porous Au matrix. An example of this type of etch-induced porous structure is illustrated in FIG. 3(b). Other Au base alloys, such as Au—Si, Au—Ge, Au—Bi, Au—Co, Au—Mo, Au—Rh, Au—Ru, Au—W, can be used as they behave in a similar way as the Au—Fe alloy. Annealing at high temperatures (e.g., at 200-600° C. for 10 min to 12 hrs) enhances the phase segregation. Another way of enhancing phase segregation is to perform sputter deposition or evaporation deposition at warm substrate temperatures, such as 150-400° C., optionally with a bias voltage applied.

FIG. 4(f) illustrates another embodiment of a process used to increase the surface area of an Au island surface comprises de-alloying. The process begins by first depositing Au—Ag, Au—Cu, or other Au base alloy layer having an Au content of about 20 to 80 wt. %, such as by sputtering or evaporation deposition, into each exposed region 44. This is followed by strong chemical etching of the non-Au metal, such as by using 30% $HNO_3$ or other etchant. Such de-alloying process removes Ag or Cu from the surface to leave behind a highly porous structure. Such de-alloying techniques, when applied to Au nano-islands in the electronic sequencing devices, results in significant surface area increases and associated improvement of biomolecule adhesion.

Shown in FIG. 4(g) is an embodiment of how Au islands having increased surface areas (such as obtained by the processes exemplified in FIGS. 4(b)-(f)) can be utilized for enhanced attachment of a biomolecule 42 such as a protein or DNA.

In various embodiments, the volume of porosity within an Au island region, characterized as branched or porous, is at least 10%, preferably at least 30%, and even more preferably at least 50%, so as to increase the surface area of the Au island at or near its top surface by at least by 20%, preferably by at least 40%, and even more preferably by at least 60% over a flat and smooth Au island structure.

Figure 5:
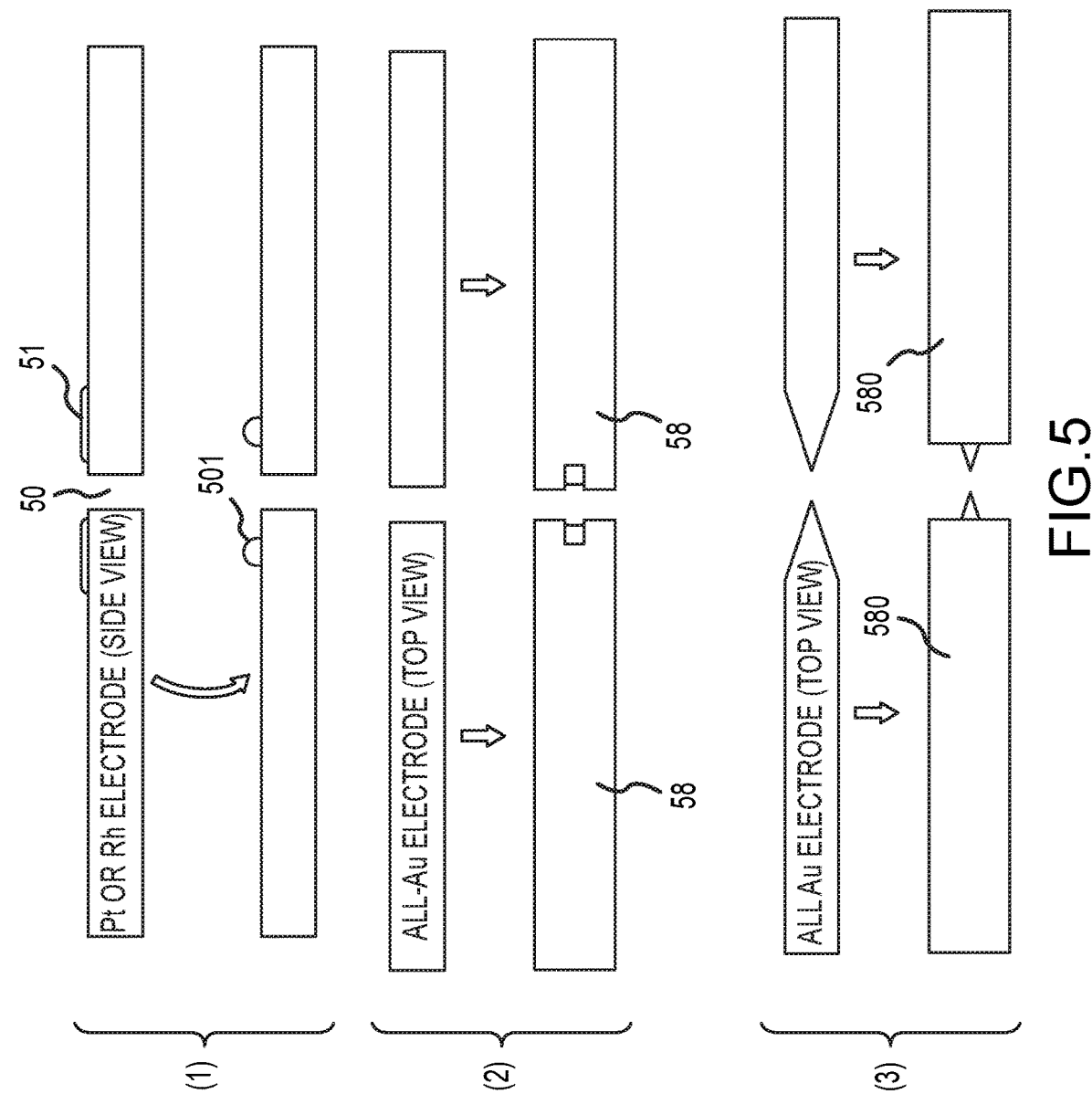
FIG. 5 illustrates methods to obtain Au islands on electrodes (Pt, Rh or Au)

With continued reference to the drawings, FIG. 5 shows three embodiments of methods to produce Au islands on electrodes such as Pt, Rh or Au. The process begins with an electrode pair separated by a nanogap 50. In each of these illustrations, the underlying substrate of the device, such as Si with $SiO_2$ insulator surface, is not shown for the purposes of clarity. A first embodiment (1) utilizes a Pt base electrode incapable of biomolecule (e.g. protein or DNA segment) attachment, so that a biomolecule adheres only to an Au island region rather than to the electrode. To obtain smaller diameter Au 501, patterned Au island 51 is heated to cause it to ball up into the smaller diameter sphere 501. An Rh electrode is also a useful option by virtue of having a lower electrical resistivity (~4.5 uΩcm for Rh, vs 9.8 uΩcm for Pt and 2.1 uΩcm for Au), and a reduced propensity for undesired biomolecule attachment. Also, Rh has no (or very small) mutual solubility with Au, unlike Pt, so alloy mixing is minimized.

A second embodiment (2) uses an all Au electrode configuration, with the Au electrode disposed in a rectangular shape but with much of the surface masked by insulator coating 58, except for an island-like region at the end of the electrode. The insulator coating may comprise polymethylmethacrylate (PMMA), polyethylene glycol (PEG), polydimethylsiloxane (PDMS), or their combinations, hydrogen silsesquioxane (HSQ), or various oxide coatings such as $Al_2O_3$, $SiO_2$ or nitride coatings such as $Si_3N_4$ coating.

A third embodiment (3) comprises the fabrication of the Au electrodes in tapered shapes having sharp tip geometry, and then masking the majority of the surface of the electrode by insulator layer 580 at all other regions except for the sharp tips of the electrodes. PEG and PDMS have remarkably non-adhesive characteristics toward proteins and cells, which can be an additional advantage for electronic sequencing devices where protein adhesion at places other than on the Au island is undesirable.

As the adhesion of biomolecules is dependent on the size of an Au island, controlling the size of Au island is critical for securing the biomolecule in sequencing devices. In various embodiments, an optimal Au island size is from about 5 to about 9 nm in diameter. Too large a diameter or too small a diameter Au island does not enable reproducible and strong adhesion of biomolecules. Thus, in various aspects of the present disclosure, techniques are shown that are used to conveniently control the Au island diameter.

Figure 6:
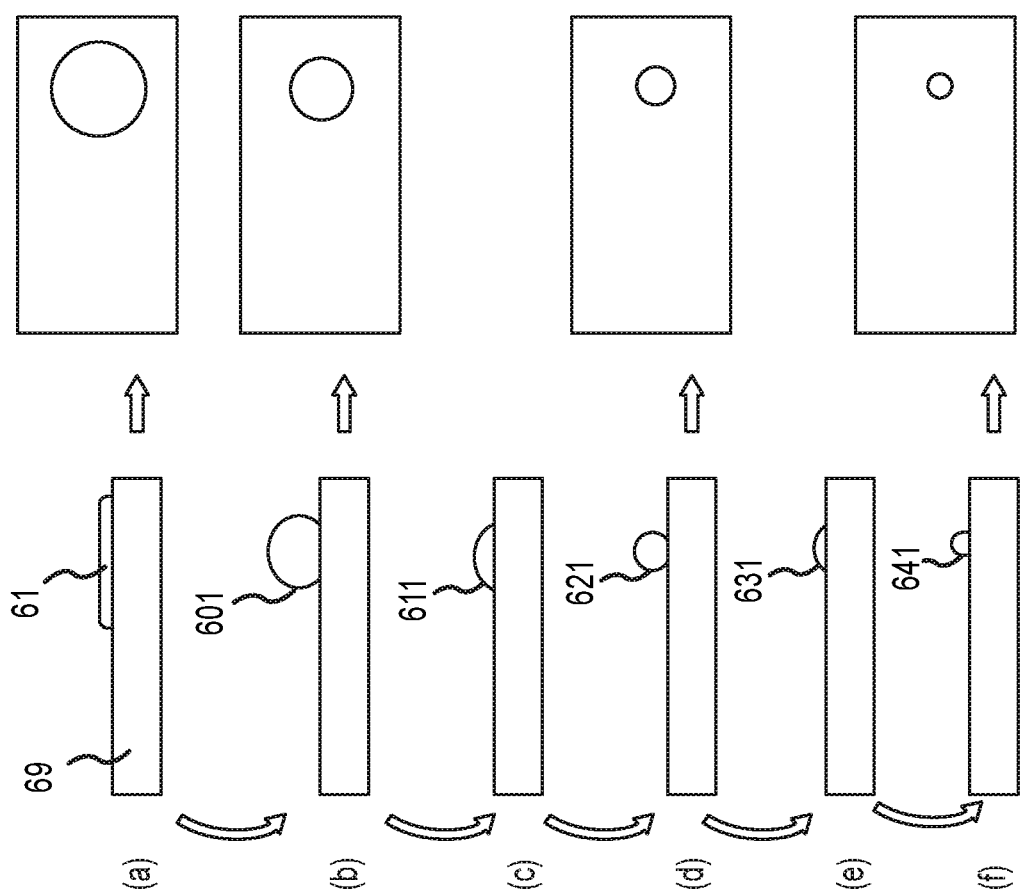
FIG. 6 illustrates progressive Au island diameter reduction by repeated spheroidization and sequential top-etching steps.

With continuing reference to the drawings, FIG. 6 illustrates a progressive Au island diameter reduction process. The method comprises repeated "spheroidization" (a balling up) and top-etching, progressing from FIG. 6(a) through FIG. 6(f). In the illustrations, only the left side electrode of each electrode pair is shown for the purposes of clarity. Further, the underlying device substrate is not shown for clarity. By employing repeated spheroidization and island top etch away processes, much smaller diameter Au islands 641 having diameters of about 5 nm to about 9 nm can be achieved more easily. In the first step of the process, a thin Au film (e.g., 1-10 nm thickness, not illustrated) is first deposited on a Pt or Rh electrode 69 by sputtering, ion beam deposition, evaporation, pulsed laser deposition, or other method, which is then nano-patterned (e.g. by nano-imprinting or other lithographic methods) to create a defined circular or oval film geometry 61 illustrated in FIG. 6(a). Subsequent annealing induces a spheroidization ball-up of the Au region into a smaller diameter Au island 601. Annealing may be at about 200 to about 400° C. for a period of time of about 10 min to 12 hrs in an atmosphere such as argon, nitrogen, forming gas type reducing atmosphere. The balled-up Au island 601 is then subjected to chemical or plasma etching for height-reduction (e.g., by ion milling, sputter etch, masking and chemical dissolution etching, etc.) to produce the flatter Au island geometry 611. Subsequent spheroidization annealing reduces the Au island diameter further and results in Au spherical islands 621. The steps of etching and spheroidization annealing are repeated again to convert the Au islands 621 to 631 and then to 641.

Figure 7A:
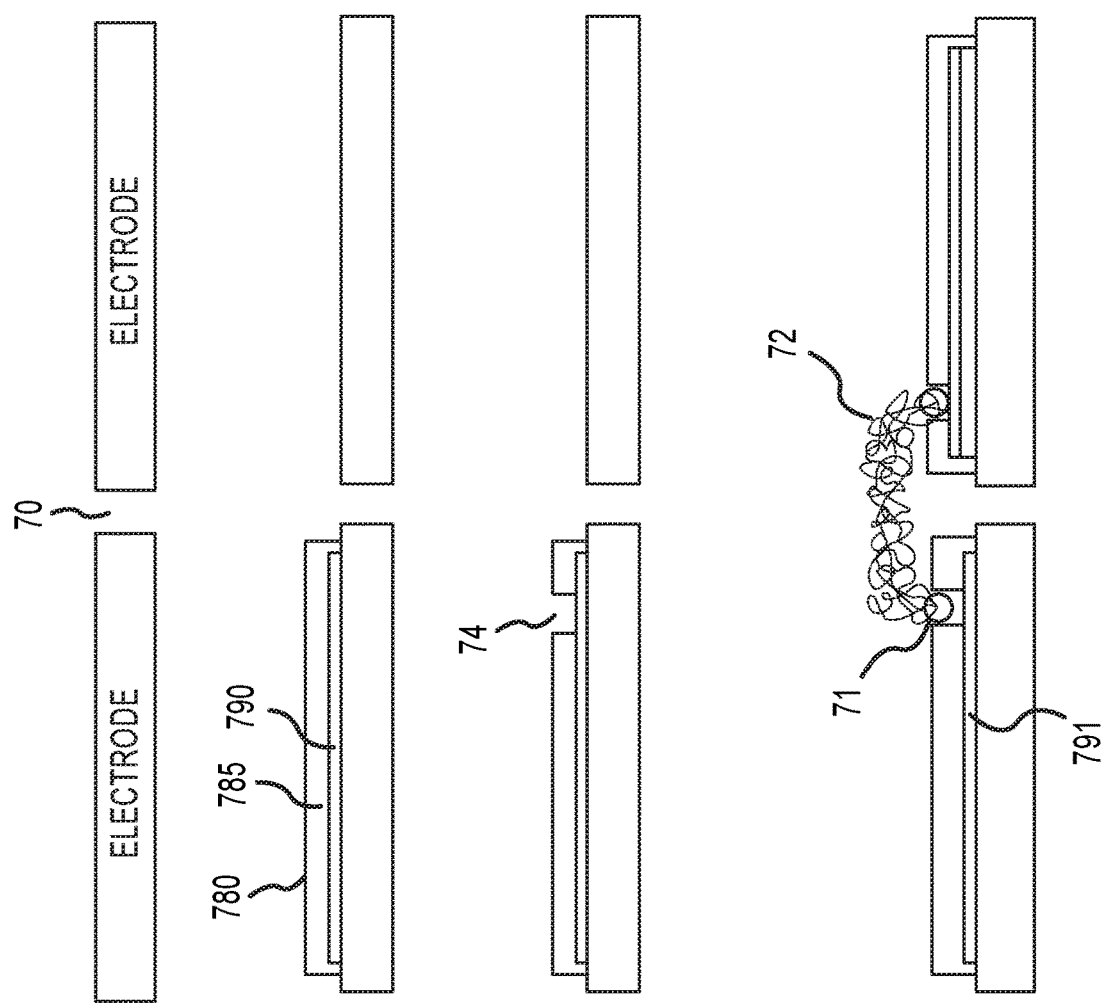
FIG. 7(a) illustrates a magnetic attraction method to securely adhere a biomolecule (protein or DNA segment) to the selected position on all the electrodes surfaces simultaneously. 7(a) illustrates magnetic attraction for secure adhesion of a biomolecule (protein or DNA segment) to the selected positions on all the Au base electrode surfaces simultaneously.

Referring to the drawings, FIG. 7(a) illustrates an embodiment of a process for forming sequencing devices in which magnetic attraction provides a more secure adhesion of a biomolecule (protein or DNA segment) to selected positions on all of the electrode surfaces simultaneously. As shown at the top of the figure, the process begins with an electrode pair having electrodes separated by a nanogap 70. A latchable magnetic stripe 785 (such as a thin film stainless magnetic alloy based on FeCrCo or FeCuNi spinodal alloys, or other corrosion-resistant magnet alloys) is deposited on the Au electrode surface 790. The magnetic hardness with coercivity (Hc) is selected to be higher than 10 Oersted (Oe) in order to guard against accidental magnetizing by a stray magnetic field, but less than 100 Oe for easier magnetization or demagnetization to attract or not attract magnetic nanoparticles. Nano-patterning of insulator spacer layer 780 is then used to create an exposed area 74 on which magnetic nanoparticles can be strongly and reliably adhered with good electrical connection.

Once the electronic sequencing device is in place, the magnetic layer is magnetized by an externally applied magnetic field, e.g., using a ferrite magnet or an electromagnet, at a field of e.g., 100-1,000 Oe. Then, using a surrounding microfluidic chamber, a liquid medium comprising biomolecules 72 already tagged with magnetic nanoparticles 71 is introduced. Biomolecules with magnetic nanoparticles bonded thereto may comprise antibody-antigen binding, streptavidin-biotin binding, peptide bonding, or electrical charge attraction, or other binding approach. A magnetic particle 71 with biomolecule 72 attached will then be attracted onto the exposed area of the magnetic stripe 791 where it will be magnetically and electrically anchored as illustrated in the lower drawing in FIG. 7(a). Optionally an intermediate Au nanoparticle may also be inserted to the biomolecule for various control purposes.

The magnetic nanoparticles to be tagged onto the biomolecules can be selected from $Fe_2O_3$, $Fe_3O_4$, or surface-protected or surface-functionalized metallic magnetic particles having higher magnetic moment than iron oxide, including Fe, Co, Ni and their alloys. The oxide-based magnetic nanoparticles are chemically stable, but the metal-based magnetic nanoparticles, while having 2-4 times higher magnetic moment, may lack the chemical stability in a liquid environment of genome sequencing. A slight surface oxidation as a protective coat against oxidation is desirable. Alternatively, the surface of magnetic nanoparticles can be Au-coated to provide chemical stability, as well as enhanced electrical conductivity and more affinity to biomolecules.

Once the desired magnetic attraction and biomolecule attachment has occurred, the liquid medium in the microfluidic chamber is washed away to remove unbonded biomolecules, and then the sequencing electronic measurements can be conducted and completed. A feature of such magnetic attachment technique is the reversibility of biomolecule attachment, i.e., easy detaching of biomolecules if needed. As the magnetic stripe (the portion of the magnetic layer on an electrode) can easily be demagnetized (e.g., by using gradually diminishing magnetic field of from 200 Oe to near zero field using a 60 Hz AC field in a few seconds), all the magnetically attached biomolecules can be thoroughly removed once the desired sequencing measurement is completed, e.g., by employing a sweeping permanent magnet to detach and collect all the magnetic particles and associated biomolecules and discarding them. In this way, the sequencing device is reusable, for example, the device can be reused at least 10 times, at least 100 times, or even at least 1,000 times.

A modified method, utilizing Pt, Pd, or Rh base electrode pairs separated by nanogap 700 instead of Au base electrodes, is illustrated in FIG. 7(b). In this method, a thin Au coating 785 is added on top of the surface of the magnetic layer 790 to enable better attachment of biomolecules. The Au layer does not noticeably affect magnetic attraction between the nanoparticle and the underlying magnetic stripe because the magnetic layer underneath is positioned very close to the exposed surface. As per the embodiment shown in FIG. 7(a), the exposed regions 740 are created by e-beam or nano-patterning of a resist layer 780. Then the device is flooded with a solution of biomolecules 720 tagged with magnetic nanoparticles 710, wherein the magnetic nanoparticle 710 bonds to the Au layer 791 and is magnetically attracted to the underlying magnetic stripe.

Figure 8:
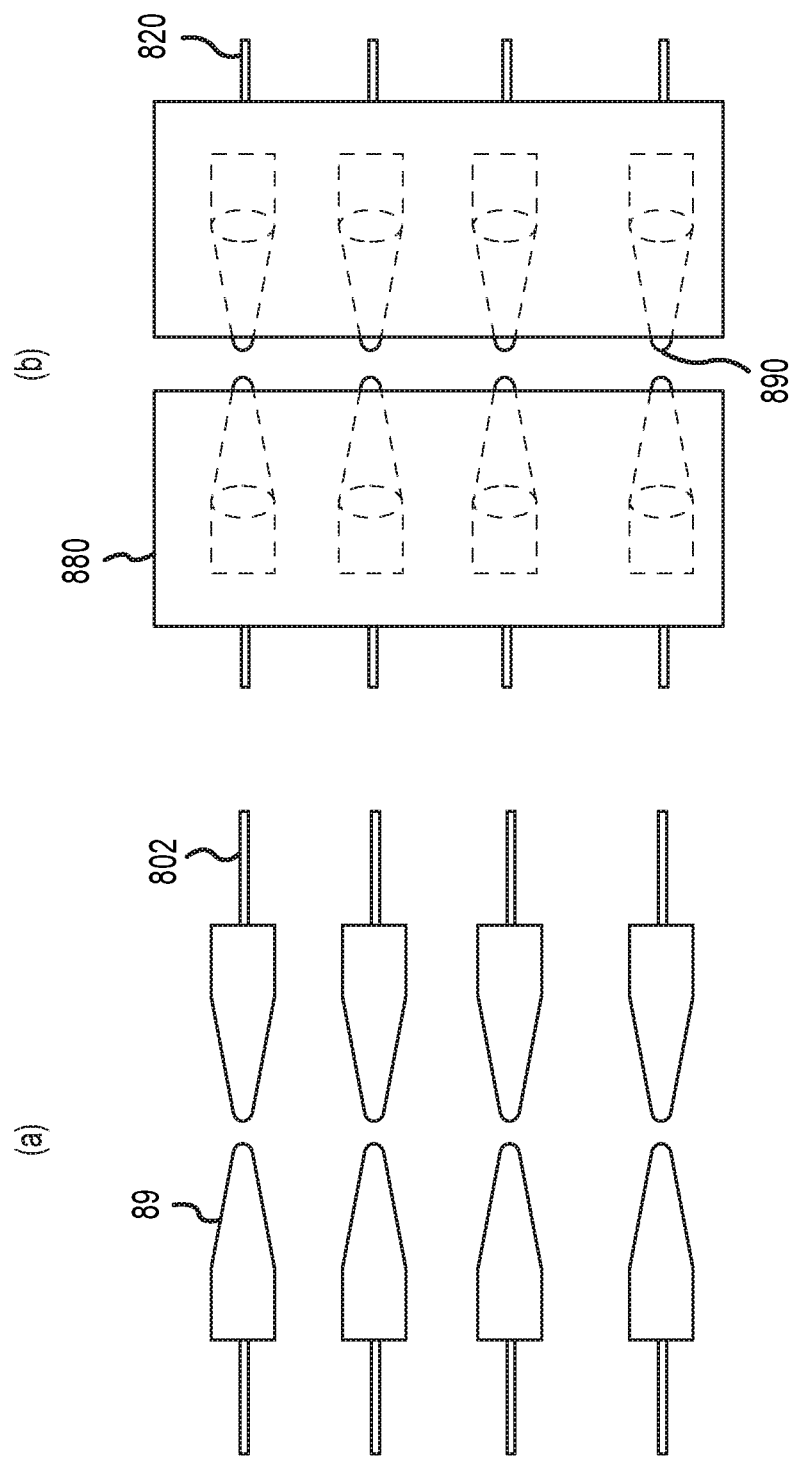
FIG. 8 illustrates a massively parallel gold-tip-exposed electrode array: (a) Tapered or sharp-tip Au electrode regions made by nano-imprinting or other lithography; (b) A structure that masks most of the Au electrode surfaces except an island position near the protruding tip to avoid unwanted biomolecule attachments on other regions of Au electrode surface.

Shown in FIG. 8 is a massively parallel Au-tip-exposed electrode array. Tapered or sharp-tip Au electrode regions 89 are first made by nano-imprinting or other lithography, with many electrode pairs in the array, as shown in FIG. 8(a). Substrate material such as Si with $SiO_2$ surface insulator is not shown for the purposes of clarity. As illustrated in FIG. 8(b), the Au electrodes 89 are then masked by a deposited mask layer 880 which is then patterned to cover the majority of the electrode surface areas except for the very tips 890 of the electrodes, in order to mitigate unwanted biomolecule attachments on other regions of the electrodes. An insulator film for this purpose may comprise, for example, PMMA, PEG, PDMS, $Al_2O_3$, $SiO_2$ or $Si_3N_4$. The desirable dimension of an Au electrode tip 890 thus left exposed is about 5-9 nm in diameter. Each electrode further comprises lead wires 802 and 820. Nano-imprinting, for the simultaneous fabrication of a large number of devices as detailed in FIG. 9, for example, more than 10,000 devices, is possible. In various embodiments, a massively parallel electrode array may comprise at least 1,000, preferably at least 10,000, and even more preferably at least 1 million devices.

Figure 9:
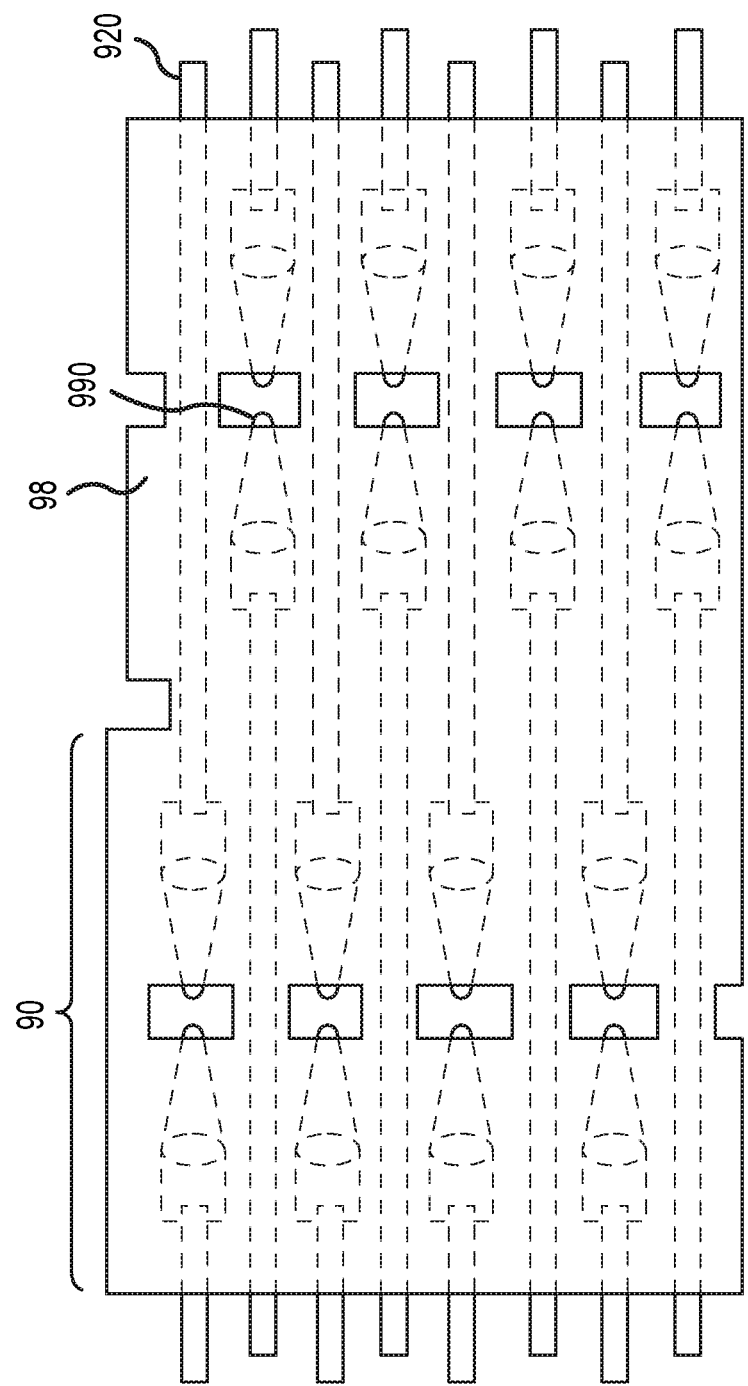
FIG. 9 illustrates an array of electrode pairs for strong adhesion of biomolecules for massively parallel, label-free detection of nucleotide attachment or detachment events (e.g., 100×100 device array or 1,000×1,000 array)

Illustrated in FIG. 9 is an exemplary array of Au nano-tip structured electrode pairs 90 for massively parallel, label-free detection of nucleotide attachment or detachment events (e.g., a 100×100 device array or a 1,000×1,000 array), with pattern-defined exposed Au electrode tips 990 (or other conductor island activated for immobilization of biomolecules) near the electrode pair gap area. The lead wires 920 can be Au or any other conductor (e.g., Ag, Cu, Pt, Pd, or Rh), insulated with a patterned top coating 98. All of the electrode pairs for label-free detection of nucleotide attachment or detachment are masked by an insulator film 98 (e.g., PMMA, PEG, PDMS, or $SiO_2$, $Al_2O_3$ or $Si_3N_4$) to cover the Au electrode surface except the electrode tips 990 as illustrated in the drawing figure. The interrogation of nucleotide attachment can be performed in real time using the array structural configuration exemplified in FIG. 9, comprising the individual lead wires 920 as shown.

Figure 10:
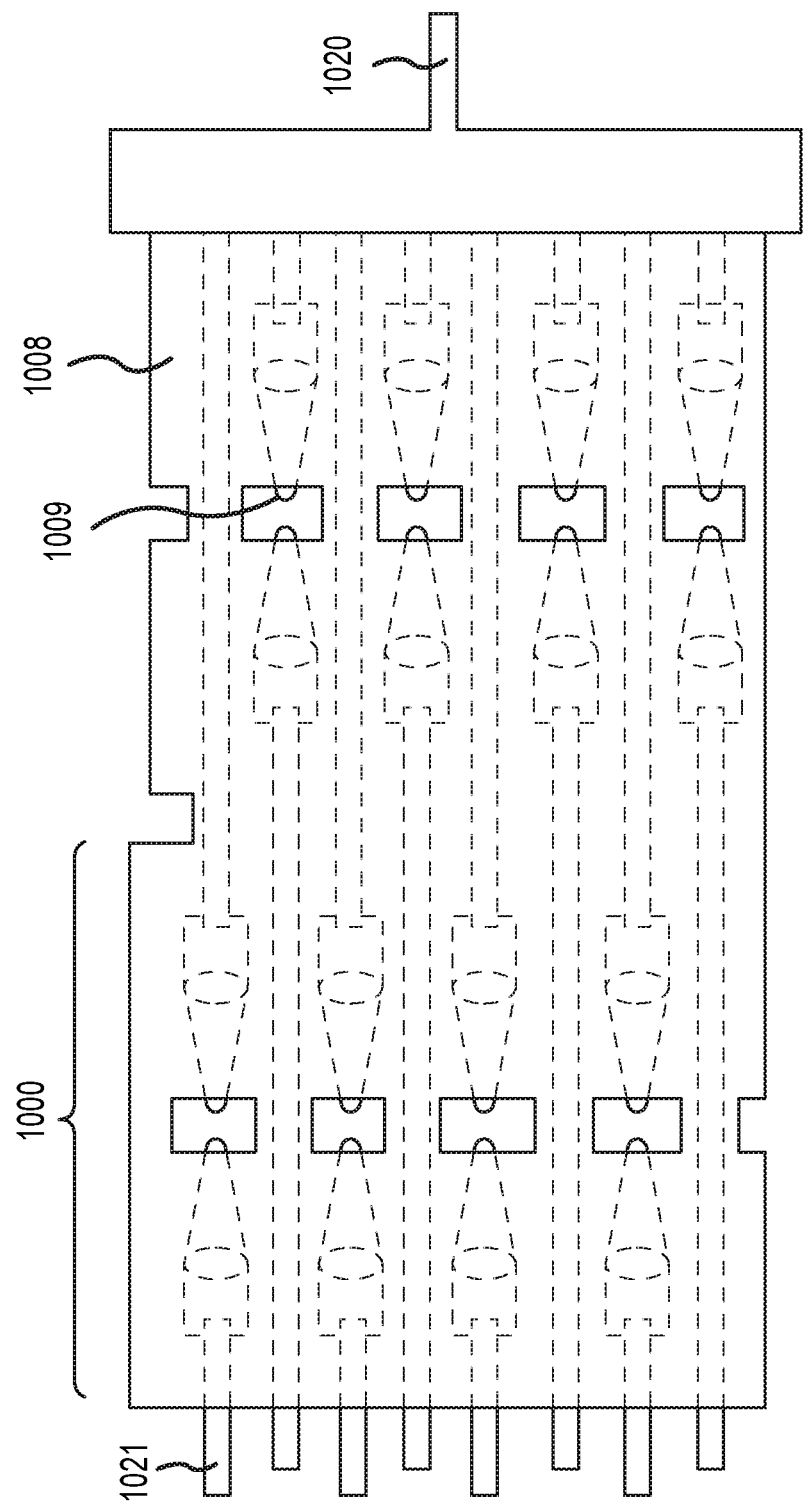
FIG. 10 illustrates a configuration for sequential interrogation of electrodes by using a common lead wire on one side of the array and wherein the left side electrodes are interrogated one at a time, sequentially.

An alternative embodiment of electronic signal interrogation is possible using the array configuration illustrated in FIG. 10. In this configuration, all the lead wires from the right side of the electrode pairs of the array of devices 1000 is shorted into a common lead wire 1020. The array also includes the insulator layer 1008 covering the majority of the electrode array except for the exposed Au tips 1009. Using the configuration depicted, interrogation of nucleotide attachment comprises performing sequential interrogation with the right side of all the lead wires shorted to a common lead 1020 and then taking turns with the individual electrical lead wires 1021 present on the left side of the pairs, one at a time, e.g., every millisecond. This method results in fewer electronic measurement complications than handling many thousands of parallel signals all at once.

Figure 11:
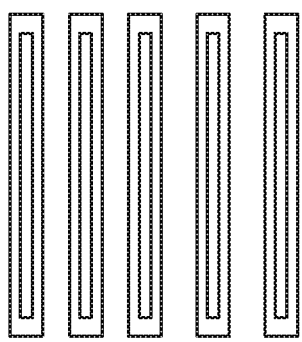
FIG. 11 illustrates a three-dimensional array of molecular electronics genome-sequencing platform. An electrically insulating top coating such as a polymer or oxide layer is applied except over the very tip gold islands.
Figure 11:
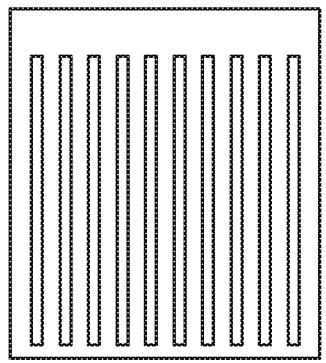
Figure 11:
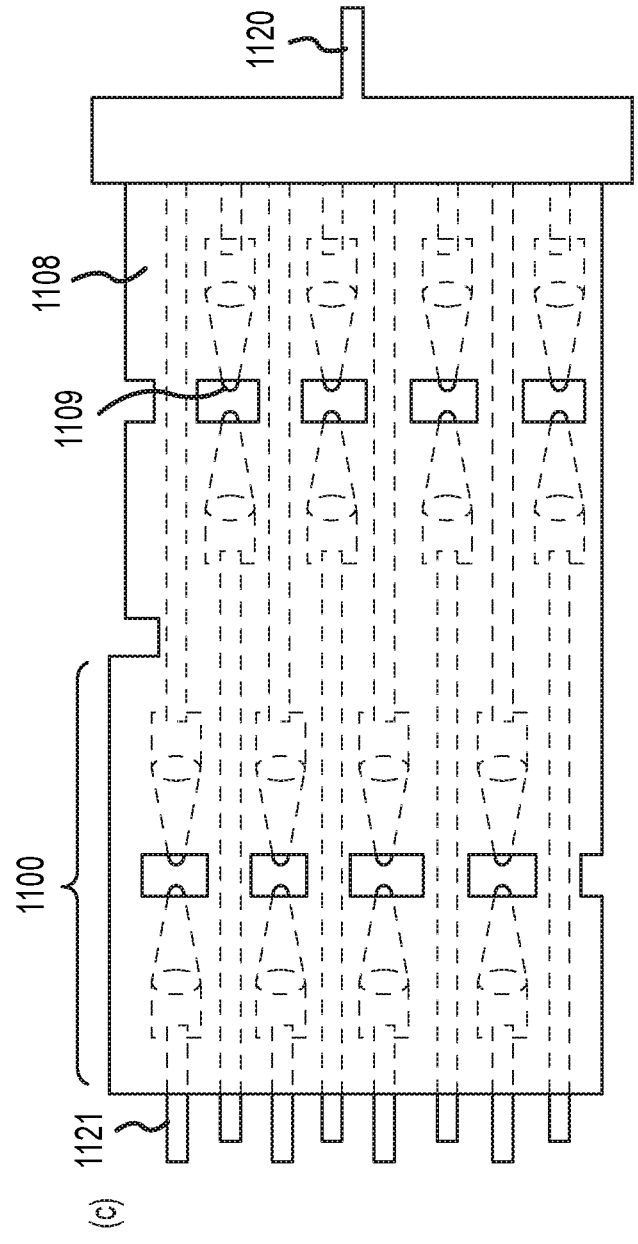

Shown in FIG. 11 is an exemplary three-dimensional array of molecular electronics genome-sequencing platform. As per the embodiments in the previous two figures, an electrically insulating top coating 1108 such as polymer or oxide layer (e.g., PMMA, PEG, PDMS, aluminum oxide, Si oxide, Si nitride, etc.) is applied and patterned to cover all the electrode surfaces in the electrode pairs 1100 except for the very tips 1109 of the electrodes. This protective coating serves as electrical insulator but also as a coating that prevents or minimizes the adhesion of biomolecules at unwanted locations. As per the configuration in FIG. 10, the right side electrode leads may be shorted into a common lead wire 1120 whilst the left side lead wires 1121 may be left singly for sequential interrogation.

Even larger data can be obtained if the FIG. 9 or FIG. 10 type aerial array sequencing structure is stacked in three dimensions, such as illustrated in FIG. 11, representing a three-dimensional array of molecular electronics genome-sequencing platform. The 3D array further comprises an accompanying microfluidic chamber for each two-dimensional array (as shown in FIG. 11(a), wherein 100 to 1,000 layers, each comprising about 10,000 devices and a microfluidic chamber), or in alternative embodiments, comprising one or more common microfluidic chambers encasing the entire three-dimensional array (as shown in FIG. 11(b), wherein 100 to 1,000 layers of sensing layers, each having about 10,000 devices, all encased in one microfluidic chamber). In such 3D configurations, at least one million to one billion devices can be operated simultaneously for extremely rapid DNA or genome sequencing. The desirable packing density of electronic sequencing pair devices is at least $10,000/cm^2$, preferably at least $100,000/cm^2$, more preferably at least $1,000,000/cm^2$, and even more preferably at least $10,000,000/cm^2$.

Figure 12:
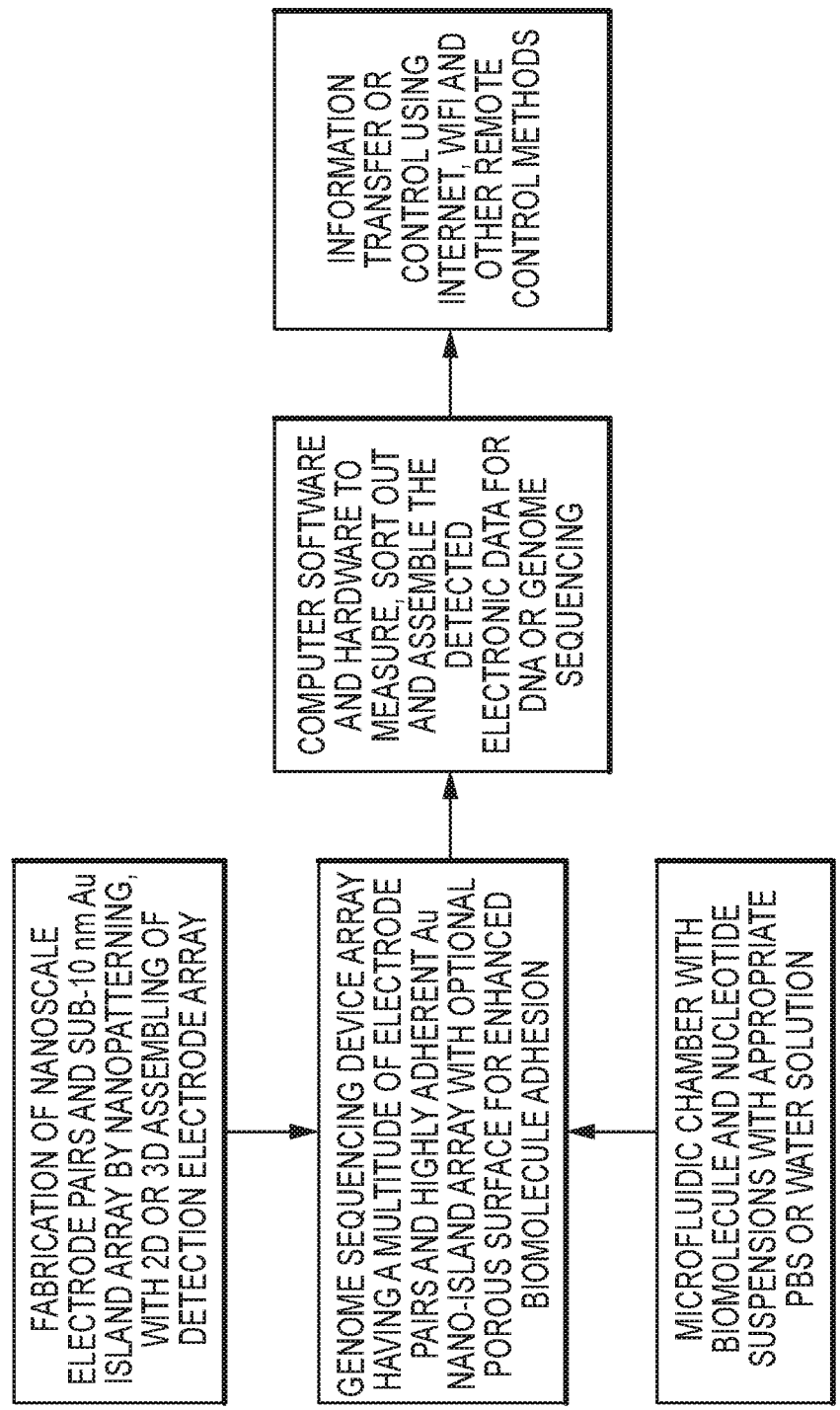
FIG. 12 illustrates a flowchart showing various aspects of a genome or DNA sequencing system according to the disclosure.

The genome or DNA sequencing structures and systems according to the disclosure is described in the flowchart of FIG. 12. Appropriate control and signal analysis/integration software and computer system are incorporated, and microfluidic system is connected to the massively parallel electronic detection system using biomolecules and coupling agents, together with DNAs and nucleotides to be sequenced.

Additional Embodiments

In various embodiments, a DNA or genome sequencing structure comprises an array of electrode pairs, each electrode in a pair separated by a nanogap and comprising a strongly adherent and highly conductive island with reduced contact resistance, and a biomolecule securely attached with each of its ends on one conductive island to bridge the nanogap, wherein the conductive islands comprise nanopattern defined Au on a Au electrode, with the Au island dimension being sub-10 nm, and further comprising electronic means of DNA or genome sequencing using DC, RF or pulse signal on nucleotide attachment, but without using fluorescent element.

In various embodiments, a non-Au electrode based DNA or genome sequencing structure comprises an array of electrodes and strongly adherent and highly conductive Au or other conductive islands having reduced contact resistance, with a biomolecule securely attached on a pair of conductive islands, with the Au island dimension being sub-10 nm, and the electrode base material selected from Pt, Pd, Rh, and Ag, with electronic means of DNA or genome sequencing using DC, RF or pulse signal on nucleotide attachment, but without using fluorescent element.

In various embodiments, the adherent conductor is made of Au, having a contact area to the electrode surface of at least 50%, and preferably %100 of the Au island diameter.

In various embodiments, the adherent gold nano-island is branched or porous with a porosity of at least 10%, preferably at least 30%, and even more preferably at least 50%, so as to increase the surface area of gold island top surface by at least by 20%, preferably by at least 40%, and even more preferably by at least 60%, over a flat and smooth Au nano-island structure.

In various embodiments, an increase in the surface area of the Au islands is obtained by one or more of the methods selected from a list of: i) plasma etching; ii) ion implantation and optional annealing heat treatment; iii) gold (Au) nano-particles attaching and bonding; iv) selective dissolving non-Au component from a nanocomposite structure; or v) de-alloying process.

In various embodiments, the structure comprises parallel devices with at least 1,000, preferably at least 10,000, even more preferably at least 1 million devices, fabricated by one or more methods selected from nano-patterning approaches such as nano-imprinting lithography, shadow mask patterning, electron beam lithography, extreme UV lithography, or X-ray lithography.

In various embodiments, the structure comprises multi-layers of devices with at least 10,000, preferably at least 1 million, even more preferably at least 100 million devices, in combination with microfluidic systems.

In various embodiments, a sequential interrogation of electrodes is enabled by a connected structure wherein one side of the device array lead wires are ganged into a common lead wire.

In various embodiments, a biomolecule is attached to an Au island using antibody-antigen coupling, streptavidin-biotin coupling, peptide bonding, thiol-gold binding, gold binding proteins, or other coupling configurations.

In various embodiments, a genome or DNA sequencing system comprises a chamber containing a multitude of biomolecule sensing devices described herein, and a microfluidic subsystem that supplies or maintains biomolecules, nucleotides, PBS or water solution, and other needed materials.

In various embodiments, the Au island diameter is progressively reduced by repeated spheroidization annealing and top-etching, with the process repeated by at least 2 cycles of spheroidization and part of the top etching to reduce the height and diameter.

In various embodiments, the height reducing etching comprises chemical etching or plasma etching.

In various embodiments, the structure comprises an added magnetic layer to enhance the attachment of magnetic-particle-tagged biomolecules, with the magnetic particles based on oxide material having natural chemical stability or metallic alloy material with surface coated with thin oxide or gold for anti-corrosion protection by a factor of at least 50% reduced corrosion rate, and/or enhanced affinity to biomolecules with at least 50% increased probability of biomolecule attachment.

In various embodiments, magnetic particles are selected from $Fe_2O_3$, $Fe_3O_4$, surface-protected or surface-functionalized metallic magnetic particles having higher magnetic moment than iron oxide including Fe, Co, Ni and their alloys.

In various embodiments, the magnetic layer is magnetized or demagnetized to enable magnetically attracted attachment of biomolecules or removal and cleaning-out of attached biomolecules with a permanent magnet sweep, allowing multiple repeat operations of the sequencing devices by at least 10 times, preferably at least 1,000 times.

In various embodiments, methods of assembly, methods of operation associated with FIGS. 1-12 and specifications therein are disclosed.

In various embodiments, these device structures for DNA sequencing can be used for cancer detection and other medical uses.

In various embodiments, these devices are usable for human genome sequencing.

The embodiments described above are only to exemplify the present invention but not to limit the scope of the present invention. Any equivalent modification or variation according to the spirit of the present invention is to be also included within the scope of the present invention.

We claim:

1. A method of manufacturing a device for DNA or genome sequencing, said method comprising:
   disposing a pair of electrodes on a substrate, the electrodes separated by a nanogap;
   depositing a resist layer over the pair of electrodes;
   patterning the resist layer to create an exposed region on each electrode at or near the nanogap;
   exposing the electrodes to plasma etching or gold (Au) ion beam implantation to roughen the surface within each exposed region; and
   exposing the exposed regions to a biomolecule, wherein the biomolecule has at least first and second ends, with each end comprising a functionalization for bonding to the pair of electrodes,
   wherein the biomolecule bridges the nanogap, with the first and second ends of the biomolecule being bound to the exposed regions.

2. The method of claim 1, wherein the resist layer comprises an electrically insulating polymer or oxide coating of from about 3 nm to about 20 nm in thickness.

3. The method of claim 1, wherein the electrodes comprise gold (Au).

4. The method of claim 1, wherein the patterning comprises e-beam or nano-lithography.

5. The method of claim 1, wherein the plasma etching comprises RF plasma, DC plasma or sputter etching processes.

6. The method of claim 1, wherein the plasma etching or the Au ion beam implantation step results in an increase in the surface area of the electrode within each exposed region of at least 50% from the surface area of the exposed region prior to plasma etching or Au ion beam implantation.

7. A method of manufacturing a device for DNA or genome sequencing, said method comprising:
   disposing a pair of electrodes on a substrate, the electrodes separated by a nanogap;
   depositing a resist layer over the pair of electrodes;
   patterning the resist layer to create an exposed region on each electrode at or near the nanogap;
   exposing the electrodes to Au nanoparticles, wherein the Au nanoparticles attach to the electrode surfaces within each exposed region;
   annealing an array at from about 200° to about 500° C. to bond the Au nanoparticles to the electrode surface; and
   exposing the exposed regions to a biomolecule, wherein the biomolecule has at least first and second ends, with each end comprising a functionalization for bonding to the pair of electrodes,
   wherein each biomolecule bridges the nanogap, with the first and second ends of the biomolecule being bound to the exposed regions.

8. The method of claim 7, wherein the resist layer comprises an electrically insulating ceramic layer comprising $Al_2O_3$ or $SiO_2$.

9. The method of claim 7, wherein the electrodes comprise gold (Au).

10. The method of claim 7, wherein the patterning comprises e-beam or nano-lithography.

11. A method of manufacturing a device for DNA or genome sequencing, said method comprising:
- disposing a pair of Au metal alloy electrodes on a substrate, the electrodes separated by a nanogap;
- depositing a resist layer over the electrode pair;
- patterning the resist layer to create an exposed region on each electrode at or near the nanogap;
- exposing the electrodes to an etchant solution to selectively remove a non-Au metal from the alloy within each exposed region; and
- exposing the exposed regions to a biomolecule, wherein the biomolecule has at least first and second ends, with each end comprising a functionalization for bonding to the pair of electrodes,
    - wherein each biomolecule bridges the nanogap, with the first and second ends of the biomolecule being bound to the exposed regions.

12. The method of claim 11, wherein the Au metal alloy is selected from the group consisting of Au—Si, Au—Ge, Au—Bi, Au—Co, Au—Mo, Au—Rh, Au—Ru, and Au—W.

13. The method of claim 11, wherein the resist layer comprises an electrically insulating ceramic layer comprising $Al_2O_3$ or $SiO_2$.

14. The method of claim 13, further comprising a step of annealing at from about 200° to about 600° C. for about 10 minutes to about 12 hours to promote phase separation between the Au and non-Au metal.

15. A method of manufacturing a device for DNA or genome sequencing, said method comprising:
- disposing a pair of electrodes on a substrate, the electrodes separated by a nanogap;
- depositing a resist layer over the electrode pair;
- patterning the resist layer to create an exposed region on each electrode at or near the nanogap;
- depositing Au—Ag or Au—Cu alloy onto the electrode surface within each exposed region;
- exposing the electrodes to an etchant solution to selectively remove the non-Au metal from the alloy deposited within each exposed region; and
- exposing the exposed regions to a biomolecule, wherein the biomolecule has at least first and second ends, with each end comprising a functionalization for bonding to the pair of electrodes,
    - wherein each biomolecule bridges the nanogap, with the first and second ends of the biomolecule being bound to the exposed regions.

16. The method of claim 15, wherein the resist layer comprises an electrically insulating ceramic layer comprising $Al_2O_3$ or $SiO_2$.

17. The method of claim 15, wherein the electrodes comprise gold (Au).

18. The method of claim 15, wherein the patterning comprises e-beam or nano-lithography.

19. A method of manufacturing a device for DNA or genome sequencing, said method comprising:
- disposing a pair of electrodes on a substrate, the electrodes separated by a nanogap;
- depositing a latchable magnetic layer over the electrodes;
- depositing a resist layer over the latchable magnetic layer;
- patterning the resist layer to create an exposed region at or near the nanogap in which the latchable magnetic layer is exposed;
- exposing the electrodes to an external magnetic field or to an applied voltage to magnetize the latchable magnetic layer; and
- exposing the exposed regions to a biomolecule, wherein the biomolecule has at least first and second ends with each end tagged with a magnetic nanoparticle for attraction to the magnetized latchable magnetic layer,
    - wherein the biomolecule bridges the nanogap, with each magnetic nanoparticle held to each electrode at the exposed regions.

20. The method of claim 19, wherein the latchable magnetic layer comprises a FeCrCo or FeCuNi spinodal alloy with Hc higher than 10 Oe.

21. The method of claim 19, further comprising the step of depositing a layer of Au over the latchable magnetic layer prior to the step of patterning the resist layer.

22. The method of claim 19, wherein the magnetic layer is magnetized or demagnetized to enable magnetically attracted attachment of magnetic nanoparticle-tagged biomolecules or removal and cleaning-out of attached magnetic nanoparticle-tagged biomolecules with a permanent magnet sweep, allowing multiple repeat operations of the device.

23. A method of manufacturing a device for DNA or genome sequencing, said method comprising:
- disposing a pair of platinum (Pt) or rhenium (Rh) electrodes on a substrate, the electrodes separated by a nanogap;
- depositing a gold (Au) film measuring from about 1 nm to about 10 nm in thickness over the electrode pair;
- patterning the resist layer to create an exposed region on each electrode at or near the nanogap;
- annealing the electrodes to induce spheroidization of the Au film into Au spheres, with one sphere disposed within each exposed region;
- etching the spheres to reduce the height of the spheres;
- repeating the annealing and etching steps at least two more times; and
- exposing the Au spheres to a biomolecule, wherein the biomolecule has at least first and second ends, with each end comprising a functionalization for bonding to the Au spheres,
    - wherein the biomolecule bridges the nanogap, with the first and second ends of the biomolecule being bound to the Au spheres.

24. The method of claim 23, wherein the annealing is at from about 200° to about 400° C. for about 10 minutes to about 12 hours to cause spheroidization.

25. The method of claim 23, wherein the etching comprises at least one of ion milling, sputter etching, and masking and chemical dissolution.

* * * * *